(12) United States Patent
Mallone et al.

(10) Patent No.: US 9,091,679 B2
(45) Date of Patent: Jul. 28, 2015

(54) METHOD FOR STIMULATING ANTIGEN-SPECIFIC T CELL RESPONSES USING ACCELERATED CO-CULTURED DENDRITIC CELLS

(75) Inventors: Roberto Mallone, Paris Cedex 14 (FR); Emanuela Martinuzzi, Paris Cedex 14 (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 832 days.

(21) Appl. No.: 13/264,255

(22) PCT Filed: Apr. 13, 2010

(86) PCT No.: PCT/EP2010/054826
§ 371 (c)(1),
(2), (4) Date: Dec. 27, 2011

(87) PCT Pub. No.: WO2010/119033
PCT Pub. Date: Oct. 21, 2010

(65) Prior Publication Data
US 2012/0094865 A1 Apr. 19, 2012

(30) Foreign Application Priority Data
Apr. 14, 2009 (WO) .................. PCT/IB2009/052793

(51) Int. Cl.
*C12N 5/0783* (2010.01)
*G01N 33/50* (2006.01)
*G01N 33/68* (2006.01)

(52) U.S. Cl.
CPC .......... *G01N 33/5047* (2013.01); *C12N 5/0638* (2013.01); *G01N 33/505* (2013.01); *G01N 33/6893* (2013.01); *G01N 2800/24* (2013.01); *G01N 2800/52* (2013.01)

(58) Field of Classification Search
None
See application file for complete search history.

(56) References Cited

FOREIGN PATENT DOCUMENTS

| EP | 0922758 | 6/1999 |
| EP | 1473564 | 11/2004 |
| WO | 2008/022030 | 2/2008 |
| WO | 2009/040413 | 4/2009 |

OTHER PUBLICATIONS

Dauer et al., "FastDC derived from human monocytes within 48 h effectively prime tumor antigen-specific cytotoxic T cells," J. Immunological Methods, 302(1-2):145-155 (2005) XP005008050.
Dauer et al., "Mature dendritic cells derived from human monocytes within 48 hours: a novel strategy for dendritic cell differentiation from blood precursors," J. Immunol., 170(8):4069-4076 (2003) XP002558313.
Ho et al., "In vitro methods for generating CD8<+> T-cell clones for immunotherapy from the naïve repertoire," J. Immunol. Methods, 310(1-2):40-52 (2006) XP025158194.
Horiguchi et al., "Screening of HLA-A24-Restricted epitope peptides from prostate-specific membrane antigen that induce specific antitumor cytotoxic T lymphocytes," Clin. Cancer Res., 8(12):3885-3892 (2002) XP009075087.
International Search Report and Written Opinion in PCT/EP2010/054826, dated Aug. 23, 2010.
International Search Report and Written Opinion in PCT/IB2009/052793, dated Dec. 15, 2009.
Meidenbauer et al., "Generation of PSA-reactive effector cells after vaccination with a PSA-based vaccine in patients with prostate cancer," Prostate, 43(2):88-100 (2000) XP002595935.
Narendran et al., "Dendritic cell-based assays, but no mannosylation of antigen, improves detection of T-cell responses to proinsulin in type 1 diabetes," Immunology, 111(4):422-429 (2004) XP002595934.
Peters et al., "Dendritic cells: from ontogenetic orphans to myelomonocytic descendants," Immunol. Today., 17 (6):273-278 (1996) XP004034611.
Ramadan et al., "Generation of *Aspergillus*- and CMV-specific T-cell responses using autologous fast DC," Cytotherapy, 693):223-234 (2004) XP008125338.
Tanaka et al., "Efficient induction of specific cytotoxic T lymphocytes to tumor rejection peptide using functional matured 2 day-cultured dendritic cells derived from human monocytes," 29(5):12563-1268 (2006) XP002595936.
Zhou et al., "CD14+ blood monocytes can differentiate into functionally mature CD83+ dendritic cells," Proc. Natl. Acad. Sci. USA, 93(6):2588-2592 (1996) XP002558300.

*Primary Examiner* — Jim Ketter
(74) *Attorney, Agent, or Firm* — McAndrews, Held & Malloy Ltd.

(57) ABSTRACT

The invention relates to a method for stimulating antigen-specific T cell responses by using accelerated co-cultured dendritic cells, and to uses thereof, such as a method for diagnosing a disease and a method for producing isolated T cell clones displaying specific immunological properties.

20 Claims, 11 Drawing Sheets

Figure 1:
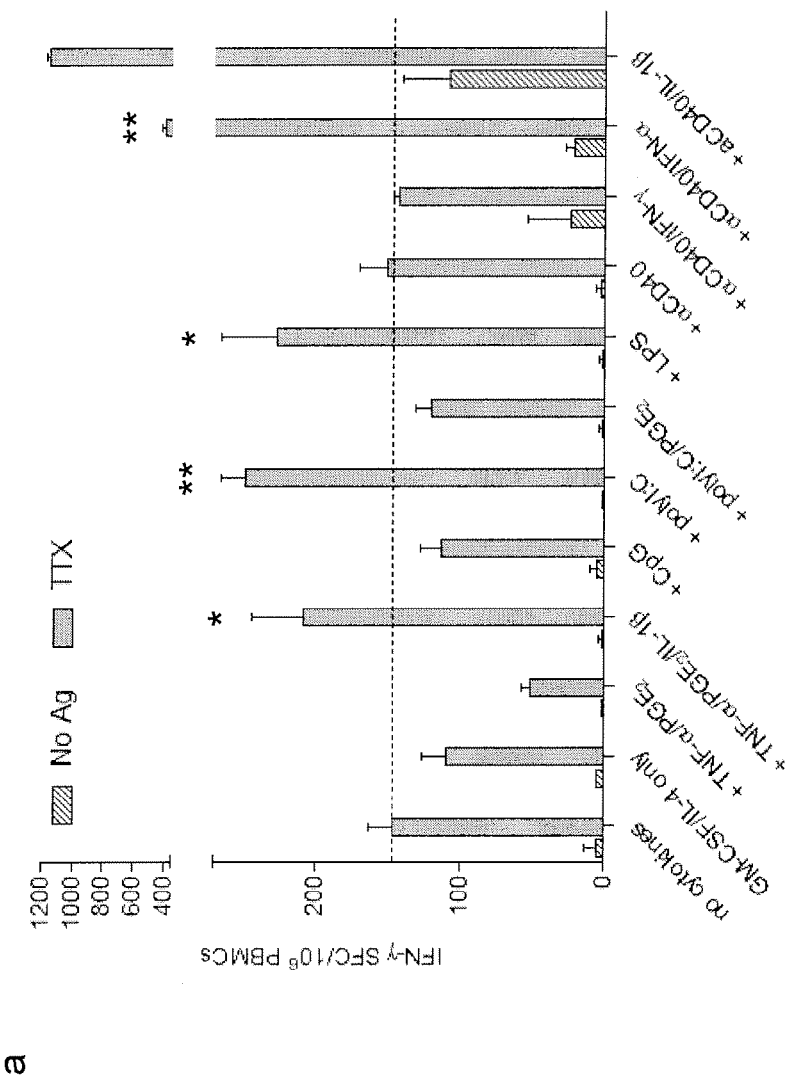
Figure 1:
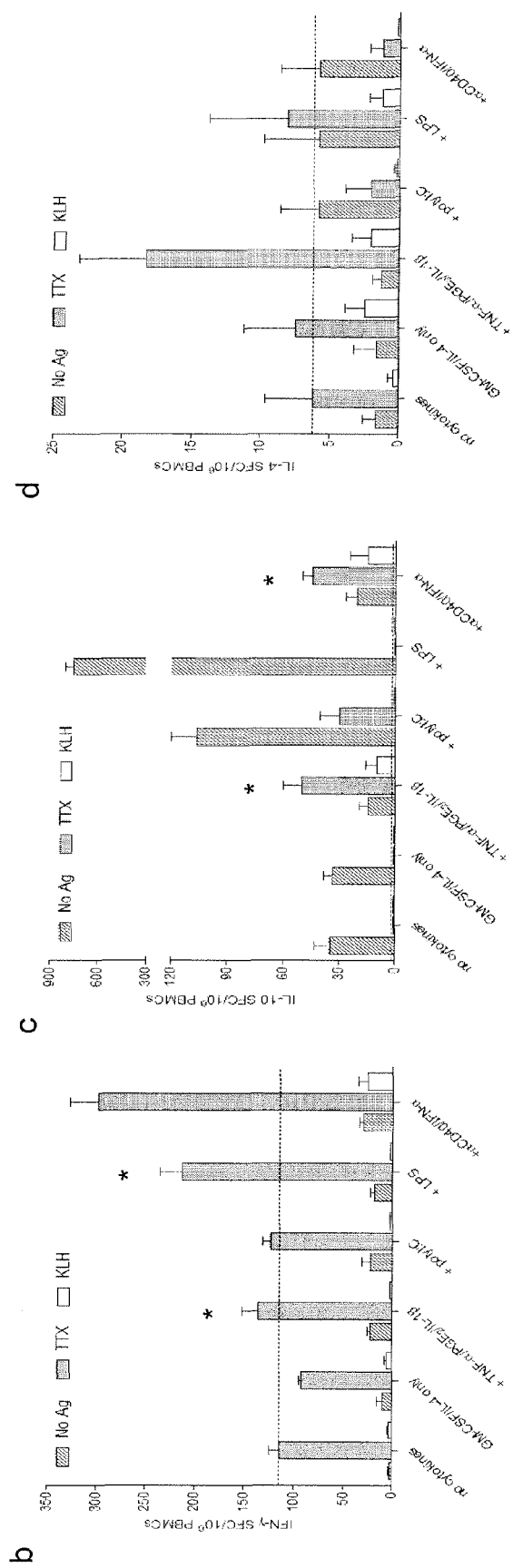

METHOD FOR STIMULATING ANTIGEN-SPECIFIC T CELL RESPONSES USING ACCELERATED CO-CULTURED DENDRITIC CELLS

The present application is filed pursuant to 35 U.S.C. 371 as a U.S. National Phase application of International Patent Application No. PCT/EP2010/054826, which was filed Apr. 13, 2010, claiming the benefit of priority to International Patent Application No. PCT/IB2009/052793, which was filed on Apr. 14, 2009. The entire text of the aforementioned applications is incorporated herein by reference in its entirety.

FIELD OF THE INVENTION

The invention relates to a method for stimulating antigen-specific T cell responses.

BACKGROUND OF THE INVENTION

Study of antigen (Ag)-specific T cell responses poses formidable technical challenges [Kern, Trends Immunol. 26:477, 2005]. This is mainly due to the fact that Ag-specific fractions are commonly represented at very low frequencies in peripheral blood, a feature which makes their detection troublesome [Mallone, Clin. Immunol. 110:232, 2004]. This detection is even more problematic when CD4+ T cells are considered, as these fractions are frequently present at even lower frequencies than their CD8+ counterparts [Homann, Nat. Med. 7:913, 2001; Seder, Nat. Immunol. 4:835, 2003].

Several detection strategies are currently available which allow to detect such Ag-specific T cells (CD4+ and CD8+) using a variety of structural or functional readouts [Kern, Trends Immunol. 26:477, 2005]. However, one drawback shared by all techniques is that Ag-specific CD4+ T cells can rarely be detected directly ex-vivo. Most commonly, these cells need to be preliminarily expanded through 5-14 d in vitro culture steps to reach the detection threshold [Mallone, Clin. Immunol. 110:232, 2004]. A number of approaches can be used for this in vitro expansion. As peripheral blood mononuclear cells (PBMCs) contain suitable numbers of CD4+ T cells as well as antigen-presenting cells (APCs; monocytes, B cells, and minute fractions of circulating dendritic cells) (DC), they can be pulsed with the peptide epitopes or protein Ags of interest and expanded with or without the addition of co-stimulatory cytokines such as interleukin (IL)-2 and IL-7.

Alternatively, monocytes can first be isolated and differentiated into immature DC with granulocyte/macrophage colony-stimulating factor (GM-CSF) and IL-4 for 5-7 days, to be subsequently matured with different proinflammatory stimuli for an additional 24-48 h [Zhou et al., Proc. Natl. Acad. Sci. USA 93:2588, 1996]. This strategy exploits the higher stimulatory potency of DCs to achieve a larger CD4+ T cell expansion. While attractive, it requires however larger starting blood volumes, as monocytes represent only ~5-15% of PBMCs, and autologous monocytes should ideally be used to avoid selection of allo-specific CD4+ T cells. T cells need therefore to be kept in culture or frozen down while monocyte-derived DC are being generated. Besides higher PBMC needs, this procedure is also longer than those relying exclusively on blood natural APCs.

Moreover, use of peptide epitopes for T-cell stimulation requires preliminary identification of those epitopes targeted by the immune response. This identification procedure is very labor-intensive, and specific for one HLA Class I or Class II allele. Thus, different epitopes have to be identified for different HLA alleles, depending on the human subjects that one wishes to study.

Of further note, it is frequently of interest not only to detect CD4+ T cells, but also to isolate and expand them for further functional profiling.

Therefore, there is still an unmet need in the art for providing a sensitive, versatile and easy-to-use method for measuring T cell responses and for isolating T cell clones, in particular CD4+ T cells.

SUMMARY OF THE INVENTION

The inventors have discovered that it is possible to stimulate Ag-specific T cell responses by co-culturing them with maturing dendritic cells directly from unfractionated whole blood or peripheral blood mononuclear cell (PBMC) samples, using appropriate cytokine cocktails and culture conditions.

Thus, the invention provides a method for stimulating antigen (Ag)-specific T cell responses in a blood sample or PBMC sample isolated from a subject, comprising the following steps:
  a) culturing said blood or PBMC sample in a medium which induces differentiation of dendritic cells (DC);
  b) optionally, maturing said DC;
wherein an Ag is added during steps a) and/or b).

The invention also relates to the use of such a method for diagnosing a disease and/or for monitoring the effects of an immune therapy in a subject.

Another aspect of the invention relates to the use of such a method for producing Ag-specific T cell clones.

Yet another aspect of the invention relates to the use of such a method for evaluating the immunogenicity of therapeutic proteins and for Ag discovery and epitope mapping analyses.

Yet another aspect of the invention relates to the use of such a method for generating Ag-specific T regulatory cells.

DETAILED DESCRIPTION OF THE INVENTION

The invention relates to a method for stimulating Ag-specific T cell responses in a blood or PBMC sample isolated from a subject, comprising the following steps:
  a) culturing said blood sample or PBMC sample in a medium which induces the differentiation of DC;
  b) optionally, maturing said DC; wherein an Ag is added during steps a) and/or b).

In one embodiment, the Ag-specific T cell responses are CD4+ T cell responses. In another embodiment, the Ag-specific T cell responses are CD8+ T cell responses.

The inventors have demonstrated that suitable biological samples for carrying out the method of the invention are a blood sample or a PBMC sample purified from whole blood using conventional density gradient separation protocols.

In a preferred embodiment, the biological sample of the invention is a PBMC sample. The term "PBMC" or "peripheral blood mononuclear cells" or "un-fractionated PBMC", as used herein, refers to whole PBMC, i.e. to a population of white blood cells having a round nucleus, which has not been enriched in a given sub-population. Typically, the PBMC sample according to the invention has not been subjected to a selection step to contain only adherent PBMC (which consist essentially of >90% monocytes) or non-adherent PBMC (which contain T cells, B cells, natural killer (NK) cells, NK T cells and DC precursors).

A PBMC sample according to the invention therefore contains lymphocytes (B cells, T cells, NK cells, NKT cells), monocytes, and precursors thereof.

Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art.

Alternatively, the biological sample according to the invention can be a blood sample.

The term "blood sample" or "unfractionated blood sample" as used herein refers to a crude blood specimen which has been isolated from a subject and collected in tubes or other containers containing an appropriate anti-coagulant (e.g., lithium heparin or sodium citrate). The blood sample is unfractionated whole blood and contains plasma and blood cells (red blood cells, white blood cells). It may be a freshly isolated blood sample (<48 h) or a blood sample which has been obtained previously and kept frozen until use.

The term "subject" as used herein refers to a mammalian, such as a rodent (e.g. a mouse or a rat), a feline, a canine or a primate. In a preferred embodiment, said subject is a human subject.

The subject according to the invention can be a healthy subject or a subject suffering from a given disease.

The term "antigen" ("Ag") as used herein refers to protein, peptide, tissue or cell preparations capable of eliciting a T cell response. In a preferred embodiment, said Ag is a protein which can be obtained by recombinant DNA technology or by purification from different tissue or cell sources. Such proteins are not limited to natural ones, but also include modified proteins or chimeric constructs, obtained for example by changing selected aminoacid sequences or by fusing portions of different proteins. In another embodiment of the invention, said Ag is a synthetic peptide, obtained by Fmoc biochemical procedures, large-scale multipin peptide synthesis, recombinant DNA technology or other suitable procedures.

In another embodiment of the invention, the Ag is a crude or partially purified tissue or cell preparation obtained by different biochemical procedures (e.g., fixation, lysis, subcellular fractionation, density gradient separation) known to the expert in the art.

Step a): Culturing the Blood Sample or PBMC Sample in a Medium Which Induces the Differentiation of DC The method of the invention comprises the step of culturing a blood sample or a PBMC sample in a medium which induces the differentiation of DC.

Suitable media for carrying out the invention are any culture medium suitable for growth, survival and differentiation of PBMCs. Typically, it consists of a base medium containing nutrients (a source of carbon, aminoacids), a pH buffer and salts, which can be supplemented with serum of human or other origin and/or growth factors and/or antibiotics, to which agents are added that induce differentiation of DC.

Typically, the base medium can be RPMI 1640, DMEM, IMDM, X-VIVO or AIM-V medium, all of which are commercially available standard media.

In the embodiment of the invention where a blood sample rather than a PBMC sample is cultured, use of such base media is dispensable, and differentiating agents can be added directly into the blood, which serves as a culture medium.

The cell culture may be performed at 37° C. in a 5% $CO_2$ atmosphere, using tissue culture incubators suitable to this end.

In a preferred embodiment, said medium comprises Granulocyte/Macrophage Colony-Stimulating Factor (GM-CSF). Typically, GM-CSF is used in an amount comprised between 1 and 10,000 U/ml, preferably between 10 and 5,000 U/ml, even more preferably at about 1,000 U/ml.

GM-CSF can be obtained from a variety of sources. It may be purified or recombinant GM-CSF. GM-CSF is commercially available from different companies, for example R&D Systems or PeproTech.

In a preferred embodiment, said medium further comprises interleukin 4 (IL-4). Typically, IL-4 is used in an amount comprised between 0 and 10,000 U/ml, preferably between 10 and 1,000 U/ml, even more preferably at about 500 U/ml.

IL-4 can be obtained from a variety of sources. It may be purified or recombinant IL-4. IL-4 is commercially available from different companies, for example R&D Systems or PeproTech.

In another preferred embodiment, said medium comprises FMS-like tyrosine kinase 3 (Flt-3) ligand. Flt-3 ligand may be used alone or in combination with GM-CSF and/or IL-4. Typically, Flt-3 ligand is used in an amount comprised between 1 and 1,000 ng/ml, preferably between 10 and 100 ng/ml.

Flt-3 ligand can be obtained from a variety of sources. It may be purified or recombinant Flt-3 ligand. Flt-3 ligand is commercially available from different companies, for example R&D Systems or PeproTech.

According to the invention, the step of incubating the blood sample or PBMC sample in a medium which induces the differentiation of DC is performed for an amount of time sufficient for enriching said blood sample or PBMC sample in DC. For the person skilled in the art, this can be easily tested by examining the relative expression of markers which are known to be expressed or not to be expressed by DC. For example, an enrichment of the blood sample or PBMC sample may be reflected by an increase in markers such as CD11c, HLA-DR, CD80 and CD86 and/or by a decrease in markers such as CD14. The specificity of expression of these markers on DC populations can be assessed by limiting the cells under analysis to selected PBMC or whole blood subsets, using a variety of gating strategies. For examples, DC may be identified as cells not expressing markers typical of other subpopulations (e.g., CD3, CD14, CD16, CD19, CD34; so called $lin^{neg}$ cells), and expressing HLA-DR.

In a preferred embodiment, said step is carried out for an amount of time t(a) comprised between t(a)min and t(a)max.

Typically, the minimal incubation for step a), t(a)min, can be about 12 hours, preferably about 16 hours, even more preferably about 18 hours, about 19 hours, about 20 hours, about 21 hours, about 22 hours, about 23 hours, even more preferably about 24 hours.

Typically, the maximum incubation for step a), t(a)max can be about 10 days, preferably about 7 days, even more preferably about 6 days, about 5 days, about 4 days, about 3 days, about 2 days, even more preferably about 1 day.

The minimal and maximal incubation times t(a)min and t(a)max disclosed above can be combined.

In a preferred embodiment, step a) is carried out for an amount of time t(a) comprised between about 16 hours and about 7 days, preferably between about 20 hours and about 4 days.

In a preferred embodiment, step a) is carried out for an amount of time t(a) of about 24 hours.

Indeed, the inventors have demonstrated that the conventional protocols for producing DC, that are subsequently capable of stimulating Ag-specific T cell responses when added to isolated T cells, using purified monocytes as starting material, can be applied to the production of DC in co-culture, and hence to the method for stimulating antigen-specific T cell responses of the invention. Such methods are described for example in Caux et al. *Nature* 360:258, 1992; Romani et al., *J Exp Med.* 180: 83, 1994 and Sallusto et al., *J Exp Med.* 179: 1109, 1994.

Moreover, the inventors have demonstrated that, unexpectedly, the accelerated protocol described by Dauer et al., [Dauer et al., *J Immunol*, 170:4069, 2003], can also be used for the method of the invention, in order to stimulate Ag-specific T cell responses, using unfractionated blood samples or PBMC samples as starting material.

Step b): Maturing the DC

According to the method of the invention, after enriching the blood sample or PBMC sample in DC during step a), said DC can be matured during step b).

In a preferred embodiment, pro-inflammatory stimuli and/or agents which mimic a viral or bacterial aggression are added to the medium of step a).

Examples of pro-inflammatory stimuli suitable for the method of the invention are, but are not limited to, tumor necrosis factor alpha (TNF-α), interleukin-1 beta (IL-1β), prostaglandin E2 (PGE2), anti-CD40 monoclonal antibodies (mAbs), CD40 ligand (CD40L) recombinant chimeric proteins, interferon-alpha (IFN-α, interferon-gamma (IFN-γ), interleukin-7 (IL-7). Such agents can be used alone or in different combinations with other pro-inflammatory stimuli or viral/bacterial mimetic agents. Examples of agents which mimic a viral or bacterial aggression suitable for the method of the invention are, but are not limited to, lipopolysaccharides (LPS), CpG oligodeoxynucleotides, polyinosinic:polycytidylic acid (poly I:C), Pam3CysSerLys4 (Pam3CSK4), imiquimod. Such agents can be used alone or in different combinations with other pro-inflammatory stimuli or viral/bacterial mimetic agents.

In one embodiment, step b) is carried out in the presence of at least one agent selected from the group consisting of TNF-α, IL-1β, PGE2, anti-CD40 antibody, IFN-α 2a, LPS, poly I:C, IFN-γ, IL-7 and mixtures thereof.

Said agent(s) are agents known to stimulate immune responses, and the skilled person will be able to select the appropriate concentrations of each agent for obtaining DC maturation while limiting non-specific T cell activation.

Also, the skilled person will easily construe that other agents which are known to stimulate DC maturation can also be used according to the method of the invention.

In a preferred embodiment, step b) is carried out in the presence of TNF-α, IL-1β and PGE2.

Typically, TNF-α is used in an amount comprised between 1 and 10,000 U/ml, preferably between 10 and 5,000 U/ml, even more preferably at about 1,000 U/ml. TNF-α can be obtained from a variety of sources. It may be purified or recombinant TNF-α. TNF-α is commercially available from different companies, for example R&D Systems or PeproTech.

Typically, IL-1β is used in an amount comprised between 0.1 and 1,000 ng/ml, preferably between 1 and 100 ng/ml, even more preferably at about 10 ng/ml. IL-1β can be obtained from a variety of sources. It may be purified or recombinant IL-1β. IL-1β is commercially available from different companies, for example R&D Systems or PeproTech.

Typically, PGE2 is used in an amount comprised between 0.01 and 100 µM, preferably between 0.1 and 10 µM, even more preferably at about 1 µM. PGE2 can be obtained from a variety of sources. PGE2 is commercially available as a product of synthesis from different companies, for example Calbiochem/Merck or Sigma.

In another embodiment, step b) is carried out in the presence of anti-CD40 (for example mAb clone G28-5) and IFN-α.

Typically, anti-CD40 mAb is used in an amount comprised between 0.1 and 50 µg/ml, preferably between 1 and 25 µg/ml, even more preferably at about 10 µg/ml. In a preferred embodiment, anti-CD40 mAb is clone G28-5. Purified G28-5 or other anti-CD40 mAbs can be produced in-house from hybridoma culture supernatants according to procedures known to those skilled in the art, or purchased from different commercial sources such as BioLegend or eBioscience.

In an alternative embodiment, anti-CD40 mAbs can be substituted with recombinant CD40 ligand molecules, synthesized either in monomeric or in multimeric form. Recombinant CD40 ligand molecules can be produced in-house using recombinant DNA methodologies known to those skilled in the art, or purchased from different commercial sources such as R&D Systems.

Typically, IFN-α is used in an amount comprised between 1 and 10,000 U/ml, preferably between 10 and 5,000 U/ml, even more preferably at about 1,000 U/ml. In a preferred embodiment, IFN-α is IFN-α2a. IFN-α can be obtained from a variety of sources. It may be purified or recombinant IFN-α. IFN-α is commercially available from different companies, for example Roche (Roferon-A), R&D Systems or PeproTech.

In another embodiment, step b) is carried out in the presence of LPS. Typically, LPS is used in an amount comprised between 1 and 10,000 ng/ml, preferably between 10 and 1,000 ng/ml, even more preferably at about 100 ng/ml. LPS can be obtained from a variety of sources. It may be purified from different bacterial strains. Suitable strains are, but are not limited to, *E. coli, K. pneumoniae, P. aeruginosa, S. enterica, S. typhosa, S. marcescens*. LPS is commercially available from different companies, for example Sigma.

In another embodiment, step b) is carried out in the presence of poly I:C. Typically, poly I:C is used in an amount comprised between 0.1 and 1,000 µg/ml, preferably between 1 and 100 µg/ml, even more preferably at about 20 µg/ml. Poly I:C can be obtained from a variety of sources. It may be synthesized using methodologies known to those skilled in the art. Poly I:C is commercially available from different companies, for example Sigma.

In preferred embodiments, a low dose of IL-7 may be added to the agents of step b). Typically, IL-7 is used in an amount comprised between 0.01 and 10 ng/ml, preferably between 0.1 and 1 ng/ml, even more preferably at about 0.5 ng/ml. IL-7 can be obtained from a variety of sources. It may be purified or recombinant IL-7. IL-7 is commercially available from different companies, for example R&D Systems or PeproTech.

According to a preferred embodiment of the method of the invention, step b) is carried out for an amount of time t(b) sufficient to mature DC. Typically, this amount of time t(b) is comprised between about 12 and about 72 hours, preferably between about 16 and about 48 hours, even more preferably for about 24 hours.

In the alternative embodiment, step b) is carried out for a shorter amount of time t(b) comprised between 0 and 12 hours.

Antigen

Without wishing to be bound by theory, it is believed that the blood sample or PBMC sample subjected to the method of the invention contains a co-culture of DC at various maturation stages (monocytes, immature DC, mature DC) and of T cells, amongst other cells.

It is believed that, within this heterogeneous population of cells, the DC will take up the Ag and present it to on their surface to the T cells, which will thereby be stimulated in an Ag-specific manner.

In a preferred embodiment, said Ag is a protein which can be obtained by recombinant DNA technology or by purification from different tissue or cell sources. Typically, said protein has a length higher than 10 aminoacids, preferably higher than 15 aminoacids, even more preferably higher than 20 aminoacids with no theoretical upper limit. Such proteins are not limited to natural ones, but also include modified proteins or chimeric constructs, obtained for example by changing selected aminoacid sequences or by fusing portions of different proteins.

In another embodiment of the invention, said Ag is a synthetic peptide. Typically, said synthetic peptide is 3-40 aminoacid-long, preferably 5-30 aminoacid-long, even more preferably 8-20 aminoacid-long. Synthetic peptides can be obtained by Fmoc biochemical procedures, large-scale multipin peptide synthesis, recombinant DNA technology or other suitable procedures. Such peptides are not limited to natural ones, but also include modified peptides or chimeric peptides, obtained for example by changing selected aminoacid sequences or by fusing portions of different proteins.

In another embodiment of the invention, the Ag is a crude or partially purified tissue or cell preparation obtained by different biochemical procedures (e.g., fixation, lysis, subcellular fractionation, density gradient separation) known to the expert in the art.

The skilled person in the art will be able to select the appropriate Ag, depending on the desired T cell stimulation.

The skilled person will also know at which step said Ag should be introduced. Typically, if the Ag is a protein or a tissue or cell preparation, it will generally be added during steps a). Typically, if the Ag is a peptide, it can be added at step b) rather than at step a). Although there is no clear aminoacid length cutoff to predict whether a given peptide will be directly bound to MHC Class II molecules or will be taken up and processed by dendritic cells prior to presentation on MHC Class II molecules, it falls within the ability of the person skilled in the art to optimize the time of addition of intermediate length peptides for each case.

Detection of the Stimulated T Cells

Methods for the detection of stimulated T cells are known to the skilled person. The procedures described below provide a few examples of suitable methods. However, the person skilled in the art can easily construe that any method suitable for assessing the stimulation of T cells in response to an Ag can be used.

Enzyme-Linked Immunospot (ELISpot):

This procedure is described in detail below, in Example 1.

Non-adherent cells from pre-culture wells are transferred to a plate which has been coated with the desired anti-cytokine capture antibodies (Abs; e.g., anti-IFN-γ, -IL-10, -IL-2, -IL-4). Revelation is carried out with biotinylated secondary Abs and standard colorimetric or fluorimetric detection methods such as streptavidin-alkaline phosphatase and NBT-BCIP and the spots counted. ELISpot readouts are then expressed as spot-forming cells (SFC)/$10^6$ PBMCs.

Supernatant Cytokine Assay:

Cytokines released in the culture supernatant are measured by different techniques, such as enzyme-linked immunosorbent assays (ELISA), BD cytometric bead array, Biorad BioPlex assay and others.

HLA Class II Tetramers:

With this procedure, Ag-reactive T cells recognizing specific peptide epitopes are detected, using either commercially available reagents (e.g., ProImmune MHC Class II Ultimers) or in-house generated ones (e.g., from Dr. G. T. Nepom, Benaroya Research Institute, Seattle, USA) [Novak et al., *J. Clin. Invest.* 104:R63, 1999].

Upregulation of Activation Markers (e.g., CD69, CD25, CD137):

With this procedure, Ag-specific T cell responses are detected by their differential expression of activation markers exposed on the membrane following Ag-recognition.

Cytokine Capture Assays:

This system developed by Miltenyi Biotech is a valid alternative to the ELISpot to visualize Ag-specific T cells according to their cytokine response. In addition, it allows the direct sorting and cloning of the T cells of interest (see below).

CD154 Assay:

This procedure has been recently described in detail [Chattopadhyay et al., *Nat. Med.* 11:1113, 2005; Frentsch et al., *Nat. Med.* 11: 1118, 2005]. It is limited to detection of Ag-specific CD4+ T cells.

CD107 Assay:

This procedure [Betts et al., *J. Immunol. Methods* 281:65, 2003] allows the visualization of Ag-specific CD8+ T cells with cytotoxic potential.

CFSE Dilution Assay:

This procedure detects Ag-specific T cells (CD4+ and CD8+) according to their proliferation following Ag recognition [Mannering et al., *J. Immunol. Methods* 283:173, 2003].

Applications of the Method

The method for stimulating Ag-specific T cell responses described in the present application is a fast, efficient, specific and versatile procedure. To summarize, the advantages as compared to traditional methodologies are:

1. Higher sensitivity;
2. Unfractionated PBMCs or even unfractionated blood can be used, either fresh or frozen. There is no need for preliminary purification steps, making the technique simpler and less demanding in terms of blood volumes;
3. No preliminary long-term expansion is required;
4. When protein Ags or tissue or cell preparations Ags are used, the whole T cell repertoire against those Ags can be detected, rather than the repertoire against a limited set of specific epitopes;
5. No limitations of HLA restriction;
6. Compatible also with peptide Ags;
7. Compatible with different readouts of T cell activation;
8. The same stimulation technique can be used to expand and subsequently sort Ag-specific CD4+ T cells and to generate CD4+ T cell lines and clones for further characterization. As such, the described method has many applications.

The invention therefore also relates to a method for diagnosing a disease in a subject comprising the following steps:
a) culturing a blood sample or a PBMC sample obtained from said subject in a medium which induces the differentiation of DC;
b) optionally, maturing said DC;
c) detecting T cell responses; wherein one or more disease-associated Ags are added during steps a) and/or b).

The invention also relates to a method for monitoring the effects of an immune therapy in a subject suffering from a disease comprising the following steps:
a) culturing a blood sample or a PBMC sample obtained from said subject in a medium which induces the differentiation of DC;

b) optionally, maturing said DC;

c) detecting T cell responses; wherein one or more disease-associated Ags are added during steps a) and/or b).

Indeed, the inventors have discovered that the method of the invention for stimulating Ag-specific T cell responses can be useful both for diagnosing a disease and for monitoring the immunological effects of an immune therapy in several settings.

In a preferred embodiment, said disease is selected from the group consisting of autoimmune diseases. This group comprises, but is not limited to, type 1 diabetes (T1D), Wegener's granulomatosis, Crohn's disease, celiac disease and multiple sclerosis.

In another embodiment of the invention, said disease is selected from the group consisting of cancer disease. This group comprises, but is not limited to, melanoma, colon cancer, renal cancer and haematological malignancies such as leukemias, lymphomas and multiple myeloma.

In another embodiment, said disease is selected from the group consisting of infectious diseases. This group comprises, but is not limited to, diseases caused by infectious agents such as *M. tuberculosis*, HIV, hepatitis C virus, cytomegalovirus, Epstein-Barr virus, influenza viruses.

In another embodiment, said disease is a graft-vs-host disease complicating bone marrow transplantation and similar procedures.

For diagnostic applications, the method of the invention can be used to detect one or more Ag-specific T cell responses which are correlated with the disease, preferably an autoimmune disease. For example, the method can be used to detect preproinsulin- or glutamic acid decarboxylase (GAD)-specific T cell responses which are correlated with type 1 diabetes.

The expression "monitoring immune therapy" as used herein refers to measurement of changes in T cell responses induced in a given subject following in vivo administration of immune modulating agents.

For monitoring applications, different types of situations are found, according to the type of disease.

In autoimmune diseases, immune modulatory therapies can be used to blunt pathological immune responses. One strategy to accomplish this result relies on non-Ag-specific interventions based on a number of immune modulatory agents. For example, agents such as cyclosporin A (Stiller et al., *Science* 223:1362, 1984; Feutren et al., *Lancet* 19:119, 1986; Bougneres et al., *Diabetes* 39:1264, 1990), Daclizumab, mycophenolate mofetil, rapamycin, interleukin-2, anti-CD3 monoclonal antibodies (Herold et al., *N. Engl. J. Med.* 346:1692, 2002; Keymeulen et al., *N. Engl. J. Med.* 352:2598, 2005), anti-CD20 monoclonal antibodies such as Rituximab (Pescovitz et al., *N. Engl. J. Med.* 361:2143, 2009), autologous non-myeloablative hematopoietic stem cell transplantation (Voltarelli et al., *JAMA* 297:1568, 2007), autologous cord blood cell infusion (Haller et al., *Diabetes Care* 32:2041, 2009), vitamin D, T regulatory cell adaptive therapies have been, are being or are likely to be tested for T1D prevention and/or intervention. A second approach relies on Ag-specific strategies, i.e., administration of a disease-related Ag in a tolerogenic form. For example, agents such as (pro)insulin (DPT-1, *N. Engl. J. Med.* 346:1685, 2002; Skyler et al., *Diabetes Care* 28:1068, 2005; Nanto-Salonen et al., *Lancet* 372:1746, 2008), GAD (Ludvigsson et al., *N. Engl. J. Med.* 359:1909, 2008), NBI-6024 (Alleva et al., *Scand. J. Immunol.* 63:59, 2006), DiaPep277 (Raz et al., *Diabetes Metab. Res. Rev.* 23:292, 2007) and combinations thereof, anti-CD3 in combination with β-cell Ags (Bresson et al., *J. Clin. Invest.* 116:1371, 2006), in vitro or in vivo DC Ag loading (Mukhopadhaya et al., *Proc. Natl. Acad. Sci. USA* 105:6374, 2008), epitope-HLA multimers (Casares et al., *Nat. Immunol.* 3:383, 2002; Masteller et al., *J. Immunol.* 171:5587, 2003; Mallone et al., *Blood* 106:2798, 2005) have been, are being or are likely to be tested for T1D prevention and/or intervention. In cancer and infectious diseases, pathogenesis is not driven by pathological immune responses, but rather by tissue cells or infectious agents which escape control by the immune system. Immune responses against cancer or infected cells/infectious agents are therefore physiological adaptations trying to counter-act disease. These physiological mechanisms can be therapeutically boosted, using either non-Ag-specific strategies (for example, cytotoxic T lymphocyte-associated antigen 4 blockade, alone or in combination with various agents, in melanoma; Yuan et al., *Proc. Natl. Acad. Sci. USA* 105:20410, 2008; Maker et al., *Ann. Surg. Oncol.* 12:1005, 2005) or Ag-specific approaches, i.e., administration (so called vaccination) of disease-related Ag(s) in an immunogenic form. These latter approaches can be pursued by administering the Ag alone or in combination with different adjuvant agents (for example, tumor-associated Ag administration in melanoma; Di Pucchio et al, *Cancer Res.* 66:4943, 2006; Peterson et al., *J. Clin. Oncol.* 21:2342, 2003); by administering DC pulsed with the Ag (for example, tumor-associated Ag-pulsed DC infusion in melanoma; Palucka et al., *J. Immunother.* 26:432, 2003; Banchereau et al., *Cancer Res.* 61:6451, 2001; Thurner et al., *J. Exp. Med.* 190:1669, 1999) or by adoptive transfer of disease-associated Ag-specific T cells (for example, tumor-associated Ag-specific T cell infusion in melanoma; Vignard et al., *J. Immunol.* 175:4797, 2005).

Therefore it is of therapeutic interest to follow the immune changes induced by such intervention. Successful interventions should translate in a decrease (in the case of autoimmune diseases) or increase (in the case of cancer and infectious diseases) of the disease-related Ag-specific T cell responses. Such changes in disease-related Ag-specific T cell responses could be either quantitative (e.g., change in the frequency of Ag-specific T cells) or qualitative (e.g., change in the phenotype and/or function of such T cells). Availability of these immune surrogate markers of clinical efficacy can be of great utility for a variety of applications. For example: better selection of patients to treat and therapeutic agents to use based on patient's immune responses (for example, GAD administration in patients presenting GAD-specific T cell responses); optimization and/or tailoring of therapeutic doses or administration regimens (for example, increase in doses/frequency of administration if no immune change is registered), thus improving the risk-to-benefit ratio; prognostic stratification of treated patients according to their probability to respond to treatment; decision of whether to treat patients again based on maintenance or not of the induced immune changes.

The method for stimulating Ag-specific T cell responses of the invention can therefore be very useful to monitor induction of these immune changes.

Step c) of detecting T cell responses can be performed as described above, for example by measuring the amount of a given cytokine which is secreted.

In a preferred embodiment, step c) of detecting T cell responses is performed by ELISpot.

The expression "disease-associated antigens (Ags)", as used herein, refers to proteins or peptides which constitute the molecular targets of an immune response. Said molecular targets are expressed by the tissue(s) or cell(s) targeted by the immune response. Expression of disease-associated Ags can be limited to the target tissue or be extended to additional body compartments. Disease-associated Ags can be initially identified as being targets of autoantibody or T cell immune responses, or based on their selective expression by the target tissue. Some examples of disease-associated protein antigens are preproinsulin (PPI), glutamic acid decarboxylase (GAD), insulinoma-associated protein 2 (IA-2), islet-specific glucose-6-phosphatase catalytic-subunit-related protein (IGRP) and zinc transporter 8 (ZnT8) for T1D; myeloperoxydase and proteinase 3 for Wegener's graulomatosis; myelin oligodendrocyte glycoprotein (MOG) and myelin basic protein (MBP) in multiple sclerosis; gliadins in celiac disease; tyrosinase, melan-A, MART-1, gp100 and NY-ESO-1 in melanoma cancer; ESAT-6 for *M. tuberculosis* infection; and gag for HIV infection.

Examples of disease-associated peptide Ags are derived from the above said protein Ags following processing by Ag-presenting cells—including DC—and presentation in the context of different HLA Class I or Class II molecules. Therefore, said peptide Ags are different depending not only on their source Ag, but also on the HLA molecules by which they are presented. For example, a list of T1D-associated peptide Ags for both mouse and human can be found in DiLorenzo et al., *Clin. Exp. Immunol.* 148:1, 2007.

The expression "disease-associated antigens" also refers to tissues or cells which constitute the targets of an immune response. Disease-associated tissues/cells can be identified as being targets of the disease based on pathophysiology and clinical presentation of said disease. Some examples of disease-associated tissues/cells are insulin-producing pancreatic beta-cells for T1D; oligodendrocytes in multiple sclerosis; intestinal epithelia in celiac disease; malignant melanocytes in melanoma cancer; *M. tuberculosis* for tuberculosis infection; and HIV for HIV infection.

The immune response mounted against disease-associated Ags can be a pathological one (i.e., in the case of autoimmune diseases) or a physiological, potentially beneficial one, aimed at limiting the consequences of another ongoing pathological process (i.e., in the case of cancer or infectious diseases). By virtue of the pathological or physiological immune responses underlying said diseases, detection of such responses can be used to diagnose these diseases, or to follow their natural or therapeutically modified evolution. By measuring disease-associated Ag-specific T cell responses, the method described herein can therefore be applied to both immune diagnosis and monitoring (e.g., immune staging, therapeutic follow-up) of said diseases.

The person skilled in the art will know how to select appropriate disease-associated Ags. Such selection is based on a wide array of strategies. Examples of such strategies for T1D-associated Ags can be found in Wenzlau et al. *Proc. Natl. Acad. Sci. USA* 2007; Peakman et al., *J. Clin. Invest.* 1999; Nepom et al., *Proc. Natl. Acad. Sci. USA* 2001; Arif et al., *J. Clin. Invest.* 2004; Toma et al., *Proc. Natl. Acad. Sci. USA* 2005; Blancou et al., *J. Immunol.* 2007; Skowera et al., *J. Clin. Invest.* 2009. Reviews of such strategies for T1D-associated peptide epitopes can be found in Di Lorenzo et al., *Clin. Exp. Immunol.* 148:1, 2007 and in Martinuzzi et al., *Ann. N.Y. Acad. Sci.* 1150:61, 2008.

Another application of the method of the invention concerns its use for the in vitro study of the immunogenicity (or tolerogenicity) of therapeutic proteins.

The term "therapeutic proteins" as used herein refers to protein or peptide compounds of any aminoacid length which are administered or are planned to be administered in vivo to human subjects to achieve a therapeutic effect. Examples of such therapeutic proteins are, but are not limited to, disease-associated Ags (as defined above), antibodies of different species (either in their native form or partially/fully humanized), cytokines, hormones or hormone analogues, coagulation factors, enzymes, bacterial or viral proteins. Such proteins are not limited to natural ones, but also include modified proteins or chimeric constructs, obtained for example by changing selected aminoacid sequences or by fusing portions of different proteins. Without wishing to be bound by theory, there are two different therapeutic settings where evaluation of immunogenicity of therapeutic proteins is of relevance.

One first therapeutic setting concerns the use of disease-associated Ags (as defined above) for in vivo administration, with the aim of inducing a tolerogenic effect (e.g., in the case of autoimmune diseases) or an immunogenic effect (e.g., in the case of cancer or infectious diseases). It is important to first evaluate in vitro the potential to achieve said desired therapeutic effect.

In other therapeutic settings, the aim is not to induce immunogenic responses of any kind to the administered protein, but rather to avoid such responses so to allow said protein to achieve the therapeutic effect for which it is designed. Example of such settings include, without being limited to, cytokine-based immune therapies, hormone replacement therapies and replacement therapies for coagulation factors (e.g., Factor VIII in Haemophilia A) or enzymatic deficits (e.g., beta-glucuronidase in mucopolysaccharidosis VII). In all these situations, mounting of immunogenic responses against the administered protein is not desirable, as this would be counterproductive for achieving the desired therapeutic effect (e.g., side effects such as cytokine release syndromes; or neutralization/degradation of the therapeutic protein).

The invention therefore also relates to a method for evaluating the immunogenicity of a therapeutic protein comprising the following steps:
  a) culturing a blood sample or a PBMC sample in a medium which induces the differentiation of DC;
  b) optionally, maturing said DC;
  c) detecting T cell responses;
wherein said therapeutic protein is added during steps a) and/or b).

Another application of the method of the invention is its use for Ag or epitope discovery (also known as "mapping"), i.e. for screening Ags and epitopes in order to select those eliciting an Ag-specific T cell response.

The term "epitope" as used herein refers to the portion of a protein Ag recognized by a T cell. Epitopes are peptides of different aminoacid length which can bind to major histocompatibility complex (MHC) Class I or Class II molecules. The peptide-MHC complex thus formed can be recognized by the T cell receptor (TCR) expressed on T cells, thus leading to T cell activation and mounting of epitope Ag-specific T cell responses.

As Ags and epitopes are the defined molecular targets of T cells, it is often relevant to precisely identify such targets to design appropriate proteins or peptides to be used for in vitro applications (e.g., detection of Ag-specific T cell responses for diagnostic, prognostic or therapeutic purposes) or for in vivo administration (e.g., Ag- or epitope-based tolerogenic therapies in autoimmune diseases; or Ag- or epitope-based vaccinations in cancer and infectious diseases). Furthermore, definition of common rules governing epitope binding to a given MHC molecule (e.g. HLA-A2, A*0201; or HLA-DR4, DR*0401) and/or triggering of TCR signalling and T cell activation is often pursued with the aim of developing computerized algorithms capable of predicting the behaviour of a given epitope. Developing of such algorithms frequently requires availability of large experimental data sets.

The invention therefore also relates to a method for screening candidate Ags and epitopes comprising the following steps:
a) culturing a blood sample or a PBMC sample in a medium which induces the differentiation of DC;
b) optionally, maturing said DC;
c) detecting T cell responses;
wherein a candidate Ag or epitope is added during steps a) and/or b).

Said candidate Ag can also be tissue(s) or cell(s) targeted by an immune response or any type of cell coated, loaded or forced to express candidate Ags or epitopes by biochemical or molecular biology techniques known to the expert in the art.

Yet another application of the method of the invention concerns its use for producing T cell clones.

Accordingly, the invention relates to a method for producing T cell clones displaying specific immunological properties from a subject comprising the following steps:
a) culturing a blood sample or a PBMC sample obtained from said subject in a medium which induces the differentiation of DC;
b) optionally, maturing said DC;
c) isolating at least one T cell displaying said specific immunological properties;
wherein an Ag is added during steps a) and/or b).

Said specific immunological properties include, but are not limited to, recognition by the isolated T cells of the Ag added during step a) and/or b). By way of example, said specific immunological properties may also include the production of IFN-γ or the ability to exert cytotoxic effects on cells presenting the recognized Ag. T cell clones producing IFN-γ or displaying cytotoxicity can be useful for example for treatment of cancer and infectious diseases.

By way of example, another possible specific immunological property can be the production of IL-10. T cell clones producing IL-10 can be used as regulatory T cells for the treatment of autoimmune diseases.

The person skilled in the art is familiar with methods for expanding said Ag-specific T cells once isolated from a blood sample or a PBMC sample. Examples of such methods, also known as T cell cloning methods, can be found in Reijonen et al., *Diabetes* 51:1375, 2002; Mallone et al., *Blood* 106:2798, 2005; Mannering et al., *J. Immunol. Methods* 298:83, 2005; Yee et al., *J. Immunol.* 162:2227, 1999; Mandruzzato et al., *J. Immunol.* 169:4017, 2002; Oelke et al., *Nat. Med.* 9:619, 2003; Skowera et al., *J. Clin. Invest.* 118:3390, 2009.

The person skilled in the art is also familiar with methods suitable to isolate said Ag-specific T cells in a viable state based on different immunological properties. For example, selection of IFN-γ- or IL-10-producing T cells may be obtained by Miltenyi cytokine capture assays. As another example, selection of cytotoxic T cells may be obtained based on upregulation of CD107 [Betts et al., *J. Immunol. Methods* 281:65, 2003].

Yet another application of the method of the invention concerns its use for generating Ag-specific T regulatory cells.

The term "T regulatory cell" as used herein refers to specialized subpopulation of T cells that act to control and suppress activation of the immune system and thereby maintain immune system homeostasis and tolerance to self Ags. Said regulatory T cells recognizing defined disease-related Ags may be used therapeutically to restore immune tolerance in pathological situations such as autoimmune and graft vs. host diseases. Efficient methods for generating high numbers of polyclonal (i.e., recognizing a large numbers of undefined Ags) T regulatory cells have been described [Putnam et al., *Diabetes* 58:652, 2009]. Nonetheless, generation of high numbers of T regulatory cells specific for a given Ag has yet to be accomplished. The method described herein may prove useful to this end.

Accordingly, the invention relates to a method for generating Ag-specific T regulatory cells displaying specific immunological properties from a subject comprising the following steps:
a) culturing a blood sample or a PBMC sample obtained from said subject in a medium which induces the differentiation of DC with tolerogenic properties;
b) optionally, maturing said DC;
c) isolating at least one T cell displaying said specific immunological properties;
wherein an Ag is added during steps a) and/or b).

Said specific immunological properties include, but are not limited to, recognition by the isolated T cells of the Ag added during step a) and/or b). By way of example, said specific immunological properties may also include: the ability to suppress proliferation, cytokine secretion, cytotoxicity and other effector functions of T cells put in physical contact or in spatial proximity with said T regulatory cells, or put in contact with supernatants from T regulatory cell cultures; the ability to produce regulatory cytokines such as IL-10, members of the transforming growth factor (TGF)-β family, IL-35, alone or in combination with non-regulatory cytokines such as IFN-γ; the ability to proliferate only in the presence of IL-2; the ability to express markers typical of T regulatory cell populations. Such markers include, but are not limited to, CD25, CD127, glucocorticoid-induced tumor necrosis factor receptor (GITR), forkhead box P3 (FoxP3), HLA-DR, cytotoxic T-lymphocyte antigen 4 (CTLA-4), CD45RA, Inducible T-cell Costimulator (ICOS).

The person skilled in the art is familiar with methods for expanding said T regulatory cells once isolated from a blood sample or a PBMC sample. Examples of such methods can be found in Putnam et al., *Diabetes* 58:652, 2009 and in Miyara et al., *Immunity* 30:899, 2009.

The person skilled in the art is also familiar with methods suitable to isolate said T regulatory cells in a viable state based on different immunological properties. For example, selection of IL-10-producing T regulatory cells may be obtained by Miltenyi cytokine capture assays. As another example, selection of CD25high CD127-negative T regulatory cells may be obtained based on cell surface staining [Liu et al., *J. Exp. Med.* 203:1701, 2006, Seddiki et al., *J. Exp. Med.* 203:1693, 2006, Putnam et al., *Diabetes* 58:652, 2009 and in Miyara et al., *Immunity* 30:899, 2009].

The term "DC with tolerogenic properties" as used herein refers to DC capable of giving rise to T regulatory cells. Said DC with tolerogenic properties can be obtained by adding cytokines possessing regulatory properties to the previously described culture protocols.

In a preferred embodiment, said regulatory cytokine is IL-10. Typically, IL-10 is used in an amount comprised between 1 and 1,000 ng/ml, preferably between 10 and 100 ng/ml. IL-10 can be obtained from a variety of sources. It may be purified or recombinant IL-10. IL-10 is commercially available from different companies, for example R&D Systems or PeproTech.

In another preferred embodiment, said regulatory cytokine is a member of the TGF-β family such as TGF-β1. Typically, TGF-β1 is used in an amount comprised between 1 and 1,000 ng/ml, preferably between 1 and 100 ng/ml, even more preferably between 1 and 10 ng/ml. TGF-β1 can be obtained from a variety of sources. It may be purified or recombinant TGF-β1. TGF-β1 is commercially available from different companies, for example R&D Systems or PeproTech.

In yet other embodiments, said regulatory cytokines are other cytokines known to exert a regulatory activity or any combination of IL-10, a member of the TGF-β family and/or other regulatory cytokines Examples of other cytokines with regulatory activity include, without being limited to, IL-5, IL-13 and IL-35.

In a preferred embodiment, step a) is carried out for an amount of time t(a) comprised between t(a)min and t(a)max.

Typically, the minimal incubation for step a), t(a)min, can be about 12 hours, preferably about 16 hours, even more preferably about 18 hours, about 19 hours, about 20 hours, about 21 hours, about 22 hours, about 23 hours, even more preferably about 24 hours.

Typically, the maximum incubation for step a), t(a)max can be about 10 days, preferably about 7 days, even more preferably about 6 days, about 5 days, about 4 days, about 3 days, about 2 days, even more preferably about 1 day.

The minimal and maximal incubation times t(a)min and t(a)max disclosed above can be combined.

In a preferred embodiment, step a) is carried out for an amount of time t(a) comprised between about 16 hours and about 7 days, preferably between about 20 hours and about 4 days.

In a preferred embodiment, step a) is carried out for an amount of time t(a) of about 24 hours.

The invention will be further described by the following examples, which are not intended to limit the scope of the protection defined by the claims.

FIGURE LEGENDS

FIG. 1. Unfractionated human PBMCs give rise to acDCs that stimulate T cells. (a) Comparison of IFN-γ ELISpot responses to TTX or control Ag obtained by maturing acDCs with different stimuli, as indicated (see Methods and Supplementary FIG. 1 for details). The dotted line marks the IFN-γ signal obtained in the absence of cytokines *p<0.03 and **p<0.001 for comparison with "no cytokine" condition in the absence of significant background increase. (b-d) Comparison of acDC maturation protocols selected above for ELISpot detection of IFN-γ (b), IL-10 (c) and IL-4 (d) responses to TTX, KLH or control Ag. Dotted lines indicate the TTX-specific cytokine signals obtained in the absence of cytokines *p<0.04 for comparison with "no cytokine" condition in the absence of significant background increase. In all panels, one representative of at least three experiments is shown.

Figure 2:
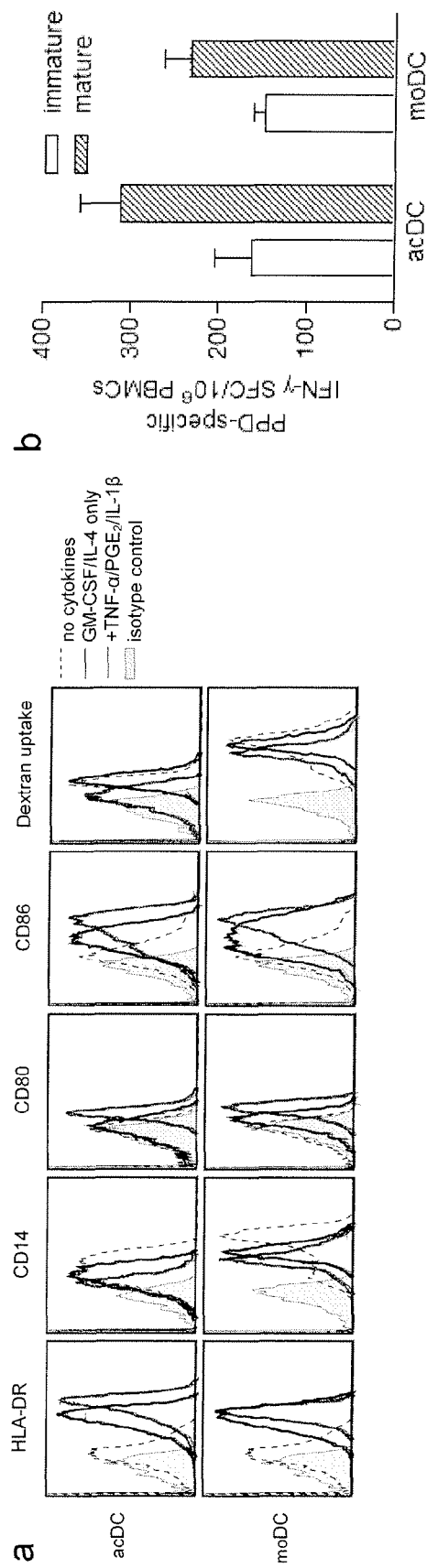
Figure 2:
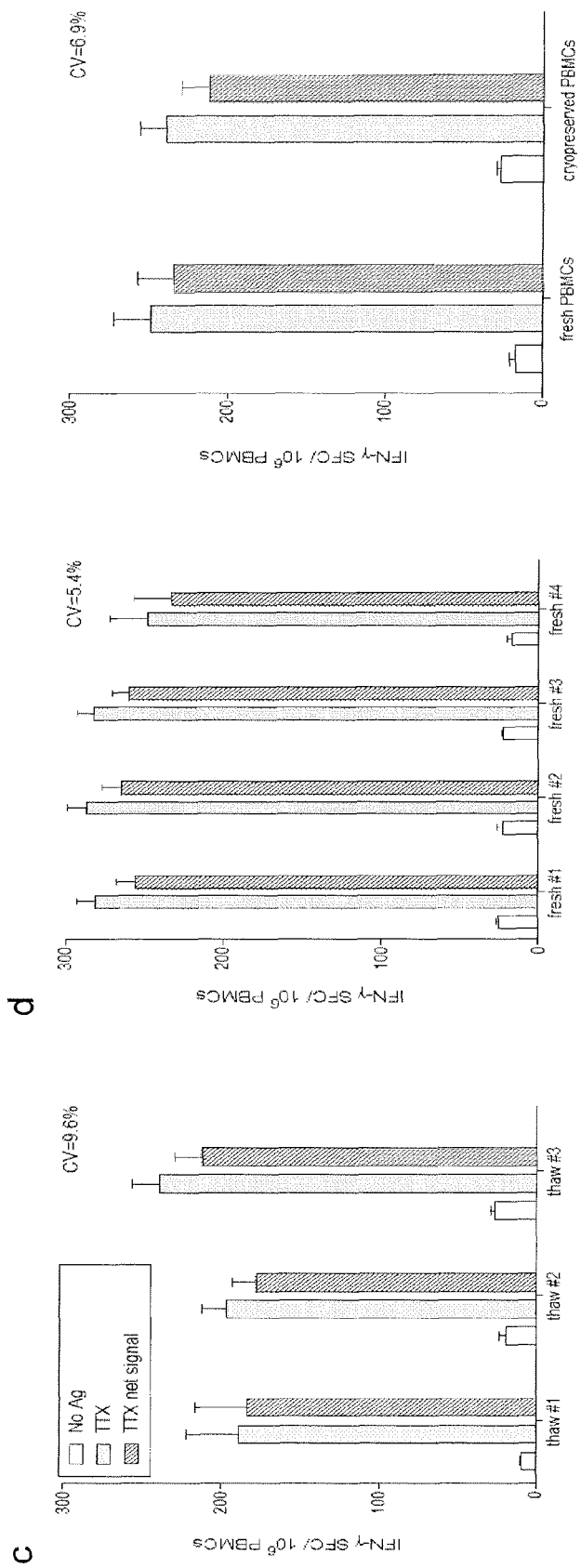

FIG. 2. Comparison between acDCs and moDCs and reproducibility of acDC-amplified IFN-γ ELISpot assays. (a) Phenotype comparison between acDCs (top) and moDCs (bottom). acDCs were obtained by culturing unfractionated PBMCs for 48 h with GM-CSF/IL-4 alone (blue profiles) or in combination with TNF-α/PGE$_2$/IL-1β (added during the last 24 h; red profiles). moDCs were generated by culturing purified monocytes for 7 d with the same cytokine cocktails (TNF-α/PGE$_2$/IL-1β added during the last 24 h). Comparisons with isotype control staining (shaded profile) and with cultures in the absence of cytokines (dotted profiles) are shown. Similar results were obtained by maturing acDCs and moDCs with anti-CD40/IFN-α (not shown). (b) Stimulatory potency in IFN-γ ELISpot assays of acDCs and moDCs matured with TNF-α/PGE$_2$/IL-1β or left immature. For acDCs, whole PBMCs (1×10$^6$/well) were cultured as before in the presence or absence of M. tubercolosis PPD for 48 h. Autologous monocytes were isolated by PBMC adherence (1×10$^6$/well) and stimulated as above for 7 d to obtain moDCs. Fresh autologous PBMCs (1×10$^6$/well) were then added onto moDCs with or without PPD for 48 h. Non-adherent cells were subsequently recovered and subjected to IFN-γ ELISpot. (c) Analytical interassay variability of acDC IFN-γ ELISpot. Three PBMC aliquots frozen from the same blood draw were thawed and tested as described. Coefficient of variation (CV)=9.6%. Basal ("No Ag") and TTX-induced IFN-γ spot counts along with net (basal-subtracted) TTX responses are indicated here and in subsequent panels d, e (acDC cultures matured with anti-CD40/IFN-α). (d) Preanalytical and analytical interassay variability of acDC IFN-γ ELISpot. PBMCs were obtained from the same individual on 4 different occasions and tested as described. CV=5.4%. (e) Variability between fresh and cryopreserved samples. PBMCs from a single blood draw were either tested fresh or frozen and subsequently tested upon thawing. CV=6.9%. All panels are representative of experiments performed in triplicate.

Figure 3:
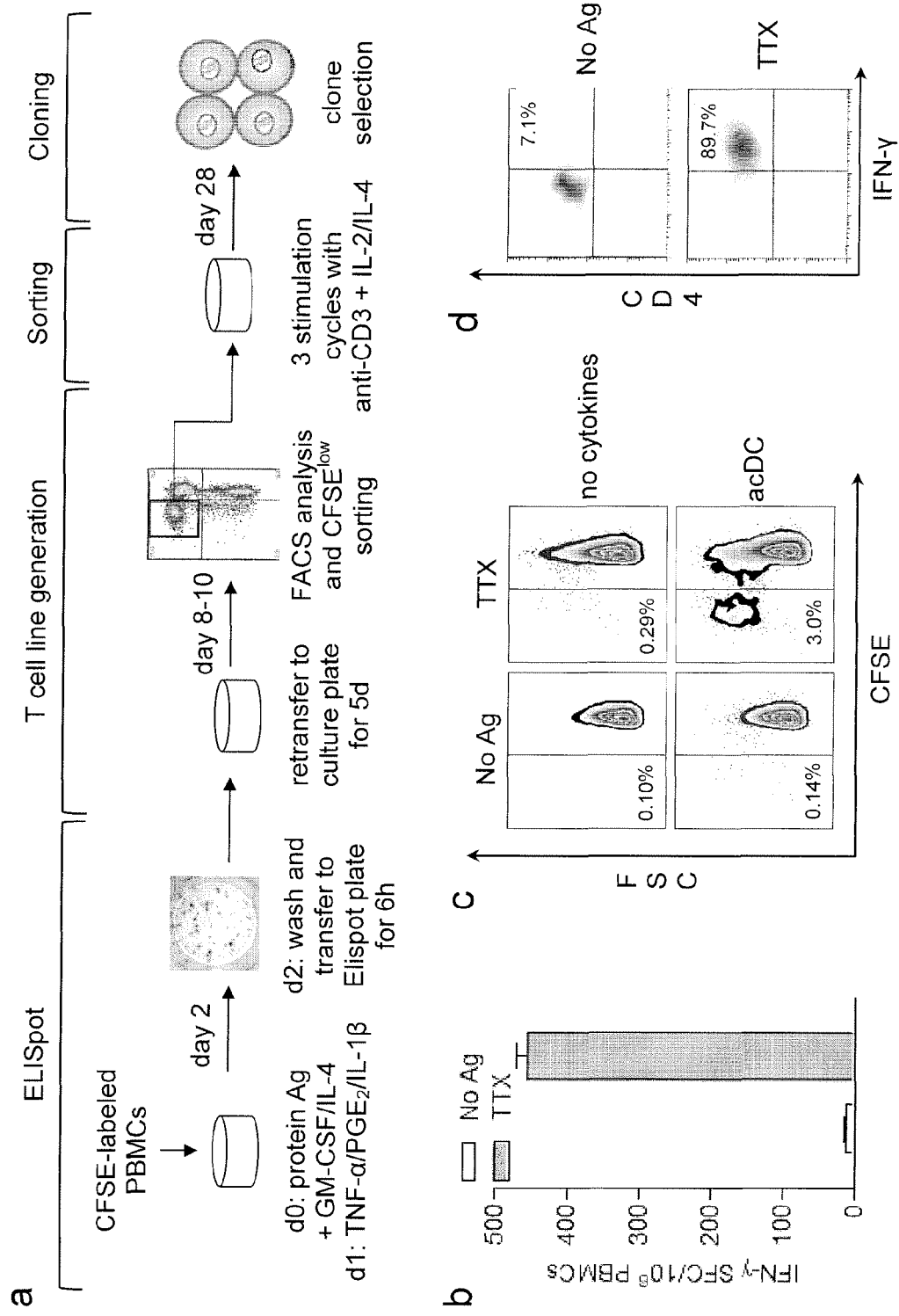

FIG. 3. acDC-expanded Ag-specific T cells can be isolated and cloned. (a) Schematic of the acDC ELISpot and T-cell clone generation procedure. acDCs were induced by adding GM-CSF and IL-4 along with protein Ag to CFSE-labeled PBMCs on day 0, followed on day 1 by TNF-α/PGE$_2$/IL-1β. On day 2, non-adherent cells were transferred into ELISpot wells for 6 h and subsequently recovered and put back into culture. Ag-specific responses were quantified by ELISpot. On day 8-10, the corresponding fraction of proliferating (CFSE$^{low}$) cells was single-cell-sorted, expanded through three stimulation cycles and tested for Ag specificity at day 28. (b) Representative acDC IFN-γ ELISpot following TTX or control stimulation. (c) CFSE proliferation of PBMCs recovered from ELISpot wells. A comparison of standard vs. acDC-driven expansion is shown. (d) The TTX-specific CFSE$^{low}$ fraction was sorted and cloned. Recall assay of one of these clones on TTX- and control-pulsed DCs by intracellular IFN-γ staining is shown.

Figure 4:
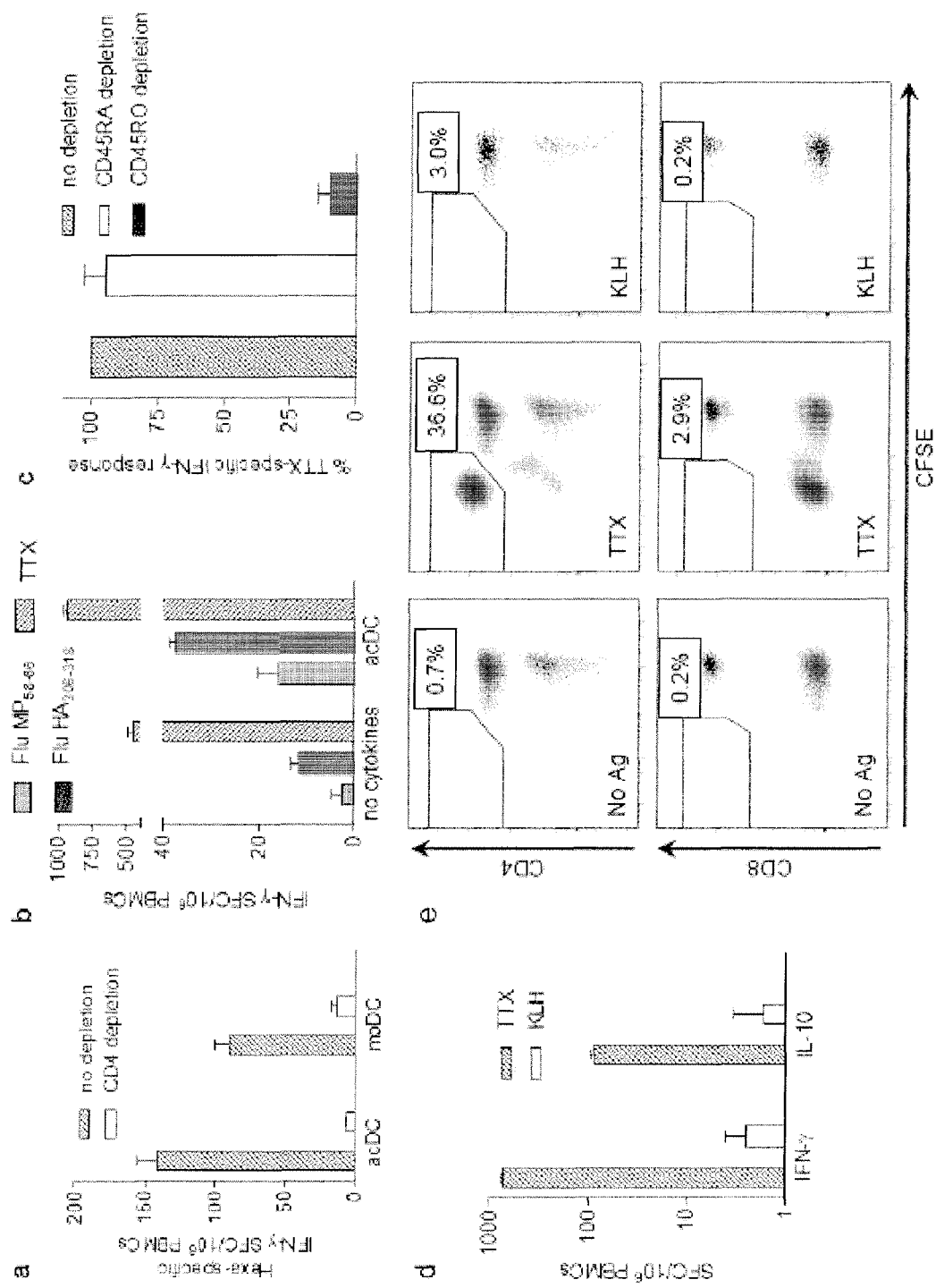

FIG. 4. Protein/peptide Ags and different stimulation periods trigger different T-cell responses. (a) acDC- and moDC-driven IFN-γ ELISpot assays were performed as in FIG. 1b on magnetically CD4-depleted or undepleted PBMCs stimulated with a hexavalent vaccine (Hexa). (b) IFN-γ ELISpot performed on PBMCs cultured with or without the acDC cocktail. PBMCs from a HLA-A2$^+$ (A*0201) –DR4$^+$ (DR*0401) subject were stimulated with the HLA-A2-restricted Flu MP$_{58-66}$ peptide, DR4-restricted Flu HA$_{306-318}$ peptide or TTX, as indicated. Peptides were added after the first 24 h of culture, while TTX was introduced ab initio. (c) TTX-specific IFN-γ ELISpot responses in acDC stimulations performed on PBMCs magnetically depleted of CD45RA$^+$ or CD45RO$^+$ cells or left undepleted. Results are expressed as relative IFN-γ responses normalized to undepleted PBMCs. (d) IFN-γ and IL-10 ELISpot responses to TTX and KLH on acDC-stimulated PBMCs labeled with CFSE. (e) CFSE-labeled PBMCs were recovered from the assay wells of panel d and cultured for additional 10 days in the absence of further stimuli and cytokines CFSE proliferation of CD4$^-$ and CD8$^+$ T cells to different Ags are shown. Stimulations in panels a-e were performed by maturing acDCs with TNF-α/PGE$_2$/IL-1β and are representative of three independent experiments (except for panel c, where means±SEM of three separate experiments are shown).

Figure 5:
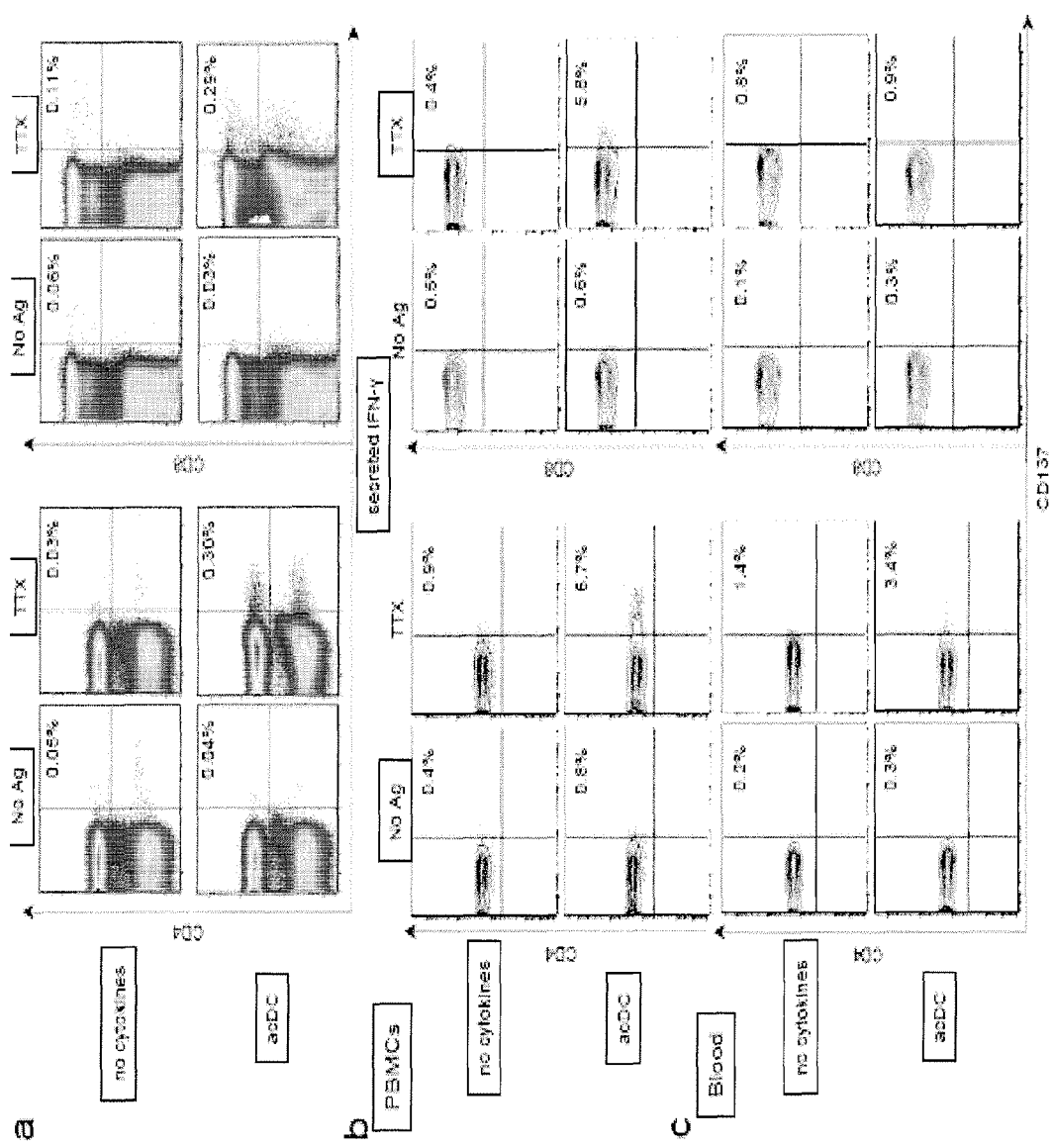

FIG. 5. Ag-specific IFN-γ secretion and CD137 upregulation are acDC-amplified in PBMCs and whole blood. (a) IFN-γ capture assay performed on PBMCs in the absence (top row) or presence (bottom row) of acDCs. After 48 h incubation, secreted IFN-γ was captured on the surface of non-adherent cells according to manufacturer's instruction. Percent numbers indicate the IFN-γ$^+$CD4$^+$ (left) or IFN-γ$^+$CD8$^+$ (right) fraction among PBMCs. (b) CD137 upregulation assays performed on purified PBMCs with (bottom row) or without (top row) acDC amplification during a 48 h culture, as above. (c) Whole blood from the same draw was stimulated in parallel by adding Ags with (bottom) or without (top) acDCs. At the end of the 48-h culture, red blood cells were lysed and samples analyzed as for panel b. Dot plots were here gated on CD4+ (left) or CD8+ (right) T cells to allow comparison between PBMCs and whole blood. Percent numbers therefore indicate the CD137− fraction among CD4+ or CD8+ T cells. Results refer to representative experiments performed in triplicate using the anti-CD40/IFN-α maturation cocktail.

Figure 6:
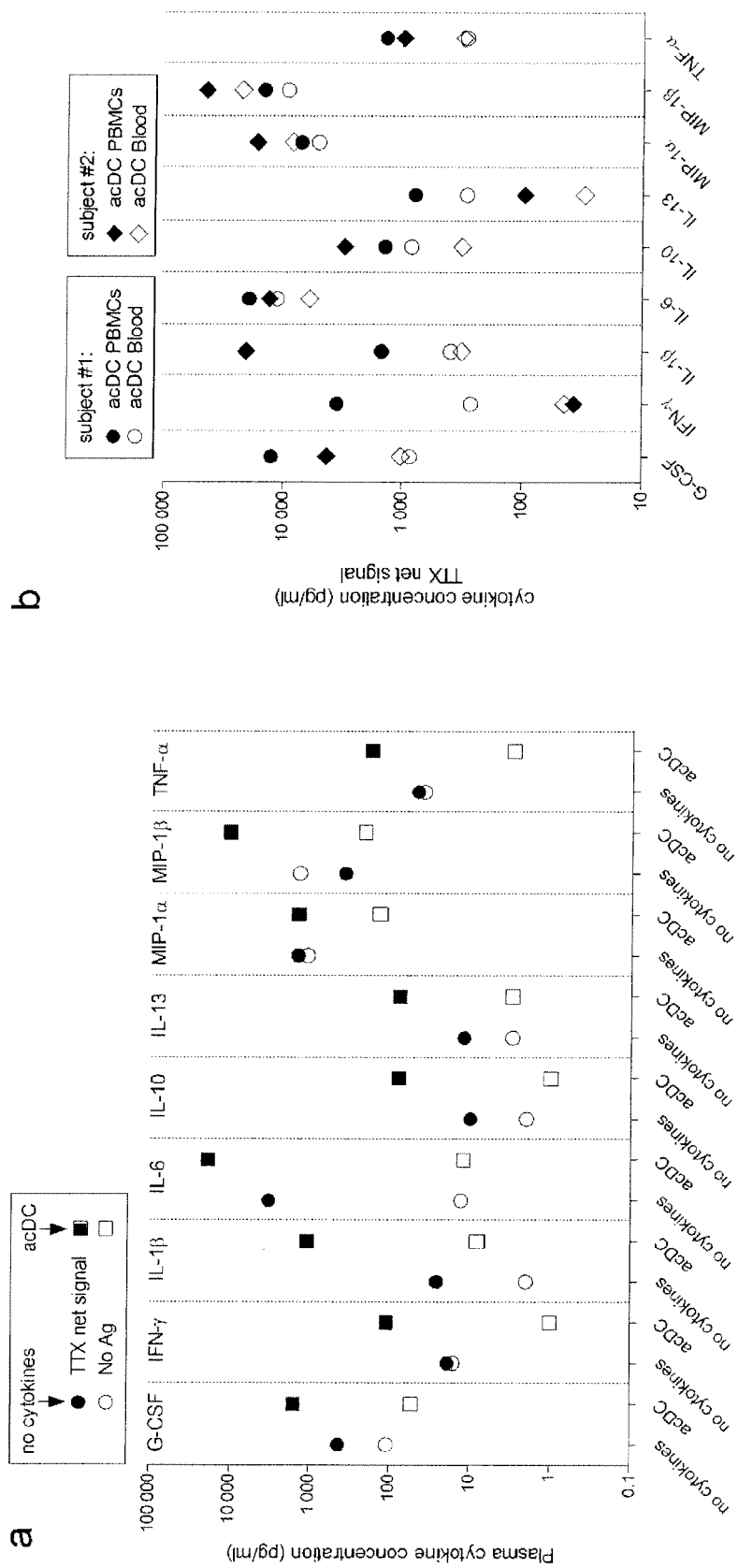

FIG. 6. acDCs amplify cytokine secretion in whole blood. (a) Whole blood (250 µl) was cultured for 48 h with or without TTX in the presence (circles) or absence (squares) of acDCs (including anti-CD40/IFN-α for maturation). Plasma supernatants were recovered and cytokines measured by Luminex bead assay. Only cytokines showing significant Ag-specific secretion are shown. Results are expressed as net TTX-stimulated cytokine concentrations (filled symbols) after subtracting basal values (represented by open symbols). (b) Comparison of PBMC (filled symbols) and whole blood (open symbols) cytokine secretion following acDC stimulation in two different subjects (circle and diamond symbols, respectively). Results are expressed as net TTX-stimulated cytokine concentrations after subtracting basal values. Representative experiments are depicted in both panels out of 10 or more performed.

Figure 7:
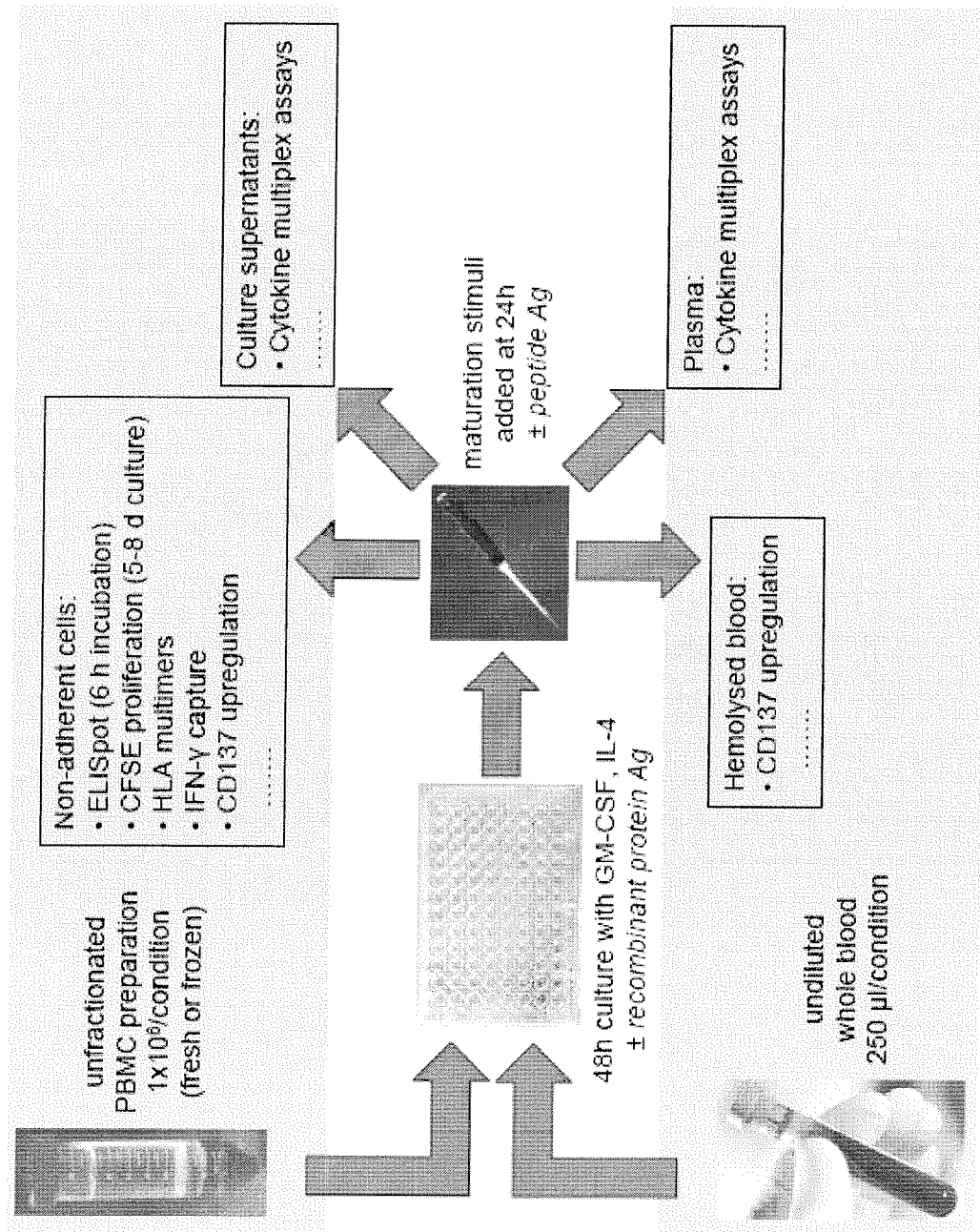

FIG. 7. Schematic of acDC-based assays. Either unfractionated PBMCs (fresh or frozen) or undiluted heparinized whole blood are incubated with GM-CSF and IL-4 for 24 h in the presence of protein Ags. Maturation stimuli are subsequently added for another 24 h, after which amplified T-cell responses can be measured by a variety of readouts. The top grey panel lists T-cell readouts tested with PBMCs; the bottom grey panel shows readouts obtained with whole blood. The acDC amplification technique is also compatible with peptide Ags, which are added at 24 h along with maturation stimuli.

Figures 8, 10:
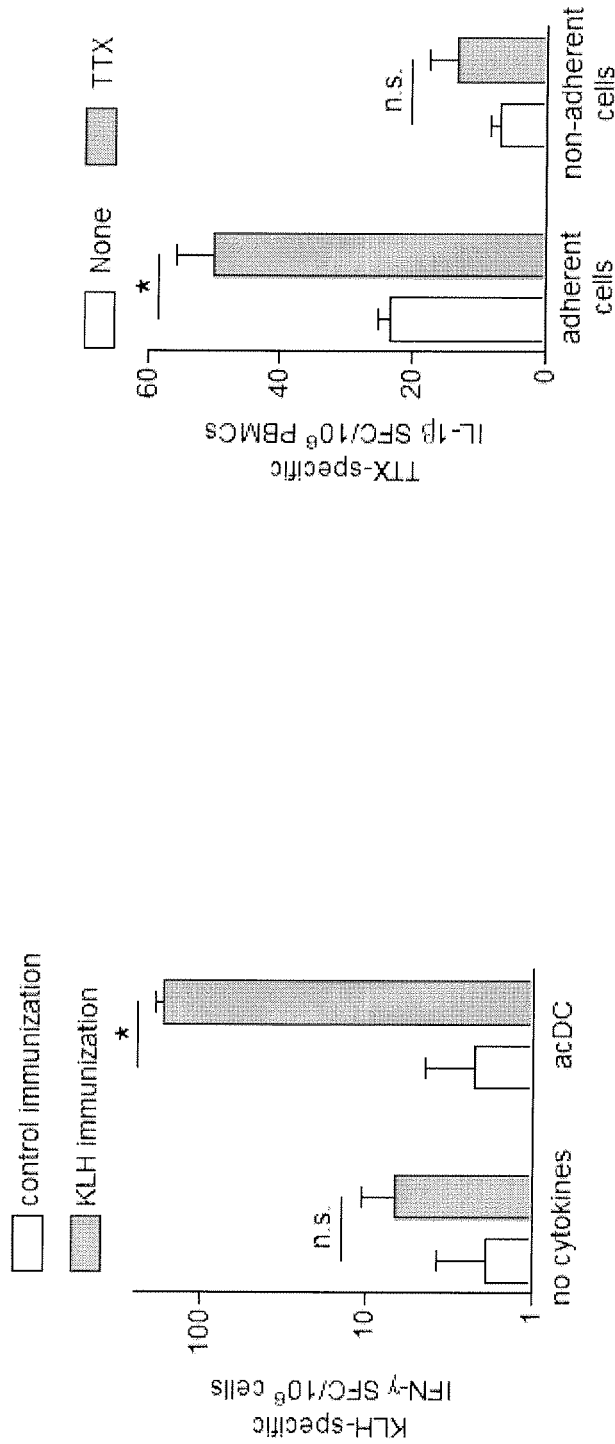

FIG. 8. acDC amplification of IFN-γ ELISpot responses in KLH-immunized mice. Balb/c mice were immunized s.c. with KLH or adjuvant alone (n=3/each) and their blood mononuclear cells ($1\times10^6$) recalled in vitro with KLH or control Ag using the acDC cocktail (LPS maturation) or no cytokines *p<0.001; n.s., not significant. Results refer to a representative experiment performed in triplicate.

Figure 9:
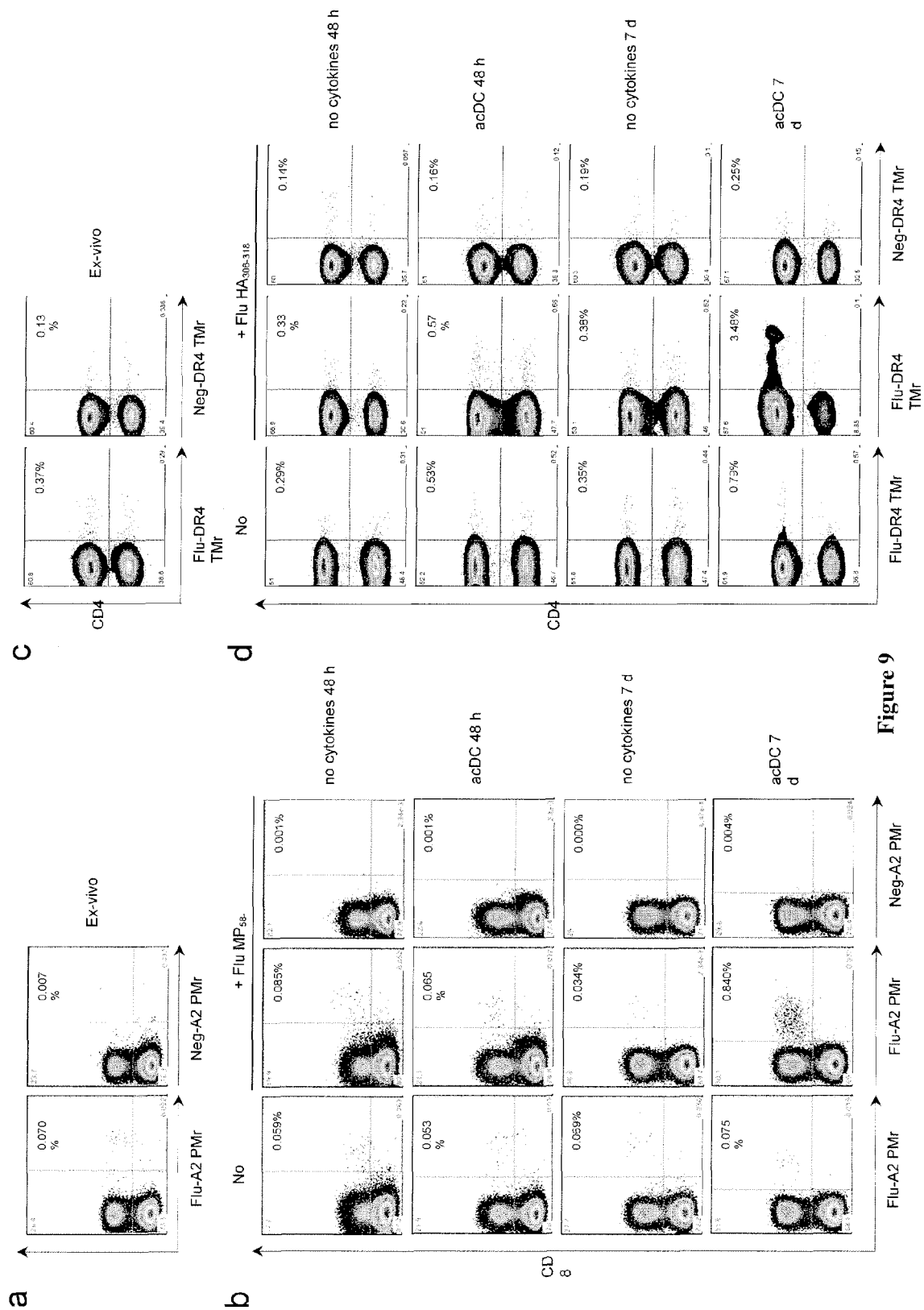

FIG. 9. acDC-driven expansion of epitope-specific T cells identified by HLA multimers. (a) Ex-vivo detection of Flu $MP_{58-66}$-specific CD8− T cells using Flu or control peptide-loaded HLA-A2 pentamers (PMrs). (b) In-vitro expansion of Flu $MP_{58-66}$-specific CD8+ T cells detected by PMrs. PBMCs were cultured without (first column) or with Flu $MP_{58-66}$ peptide (second and third columns). Cultures were carried out for 48 h (first and second row), or non-adherent cells were washed, replated and further cultured until day 7 (third and fourth row). These cultures were carried out with or without the acDC cocktail, as indicated. Flu-specific CD8+ T cells were identified with the corresponding HLA-A2 PMrs (first and second column), and background staining determined with control PMr (third column). (c,d) The same experiment was performed to detect Flu $HA_{306-318}$-specific CD4+ T cells using Flu or control peptide-loaded HLA-DR4 tetramers (TMrs). acDC maturation was induced with anti-CD40/IFN-α. Results are representative of three independent experiments.

FIG. 10. acDC-amplified IL-1β secretion is derived from adherent cells. PBMCs were stimulated with TTX or no Ag following the acDC procedure (anti-CD40/IFN-α maturation). After 48 h, adherent and non-adherent cells ($2\times10^5$/well) were tested separately in IL-1β ELISpot assays for 6 h. *p<0.01; n.s., not significant. Results refer to a representative experiment performed in triplicate.

EXAMPLES

Example 1

PBMC-Derived Accelerated Co-Cultured DC (acDC) Amplify the Ag-Specific Responses of Co-Cultured T Cells—Protein Ag Stimulation Material and Methods:

On day 0, whole PBMCs ($2.5\times10^6$ cells/well) were plated into 48-well plates in AIM-V medium (Invitrogen) supplemented with 1,000 U/ml GM-CSF, 500 U/ml IL-4 (both from R&D Systems), and relevant protein Ags (10 µg/ml). The protein antigens tested were tetanus toxoid (TTX), *M. tubercolosis* purified protein derivative (PPD), exavalent vaccine Infanrix hexa (GlaxoSmithKline), proinsulin (PI), glutamic acid decarboxylase (GAD), insulin C-peptide, pre-PI leader sequence, myeloperoxidase, proteinase 3. An example of protein used as negative control is bovine serum albumin (BSA).

On day 1, pro-inflammatory stimuli were added to induce DC maturation.

Several maturation protocols were developed and tested as detailed below.

Maturation protocol A: 1000 U/ml TNF-α, 10 ng/ml IL-1β (both from R&D) and 1 µM $PGE_2$ (Calbiochem).

This is the same cytokine cocktail used for obtaining FastDC [Dauer et al., *J. Immunol.* 170:4069, 2003], and has been described by several other groups to generate conventional (7 day) DC. In addition, we added low-dose IL-7 (0.5 ng/ml; R&D), which we have previously described to greatly amplify CD8+ T cell responses in an Ag-specific fashion (i.e., without increasing background) using an ELISpot detection system [Martinuzzi et al., *J. Immunol. Methods* 333:61, 2008].

This protocol was suitable to detect Ag-specific CD4+ T cell responses producing for example IFN-γ, IL-10, IL-2, IL-4.

Maturation protocol B: anti-CD40 monoclonal antibody (mAb; clone G28-5, 10 µg/ml), IFN-α2a (Roferon-A, Roche; 1,000 U/ml).

A similar maturation cocktail has been described for conventional 7 d DC [Luft et al., *Int. Immunol.* 14:367, 2002]. In addition, we used low-dose IL-7 (0.5 ng/ml) to further amplify responses.

This protocol was suitable to detect Ag-specific CD4+ T cell responses producing for example IFN-γ and IL-10.

Maturation protocol C: LPS 100 ng/ml and low-dose IL-7 (0.5 ng/ml).

This protocol was suitable to detect Ag-specific CD4+ T cell responses producing for example IFN-γ, but not IL-10, due to a large increase in basal (unstimulated) IL-10 secretion.

Maturation protocol D: poly I:C 20 µg/ml and low-dose IL-7 (0.5 ng/ml).

This protocol was suitable to detect Ag-specific CD4+ T cell responses producing for example IFN-γ, but not IL-10, due to a large increase in basal (unstimulated) IL-10 secretion.

T cell detection procedure: ELISpot. Non-adherent cells were washed, resuspended in fresh AIM-V medium and distributed in triplicate wells ($0.3\times10^6$ cells/well) of 96-well PVDF plates, which had been coated overnight with the desired anti-cytokine capture Abs (e.g., anti-IFN-γ, -IL-10, -IL-2, -IL-4; all from U-CyTech). No further Ags or cytokines were added, and the plates were incubated for 6 h at 37° C., 5% $CO_2$. Revelation was carried out with biotinylated secondary Abs and standard colorimetric detection such as streptavidin-alkaline phosphatase and NBT-BCIP. Spots were counted on a Bioreader 5000 Pro S-F (BioSys) ELISpot reader or equivalent, and means of triplicate wells calculated. All ELISpot readouts were expressed as spot-forming cells $(SFC)/10^6$ PBMCs. The cut-off for a positive response was set at 3SD above the average basal reactivity (i.e., reactivity against BSA or no Ag).

Phenotypic Analysis of acDC:

Phenotypes of acDC and conventional (7 day, monocyte-derived) DCs—either immature or mature—was determined by staining with mAbs specific for HLA-DR, CD14, CD80, CD86, CD11c. Endocytotic activity was assessed by incubation with dextran-FITC and subsequent evaluation of uptaken fluorescence. All cells were analyze on a FACSAria flow cytometer (BD).

Results:

Characterization of acDC revealed a phenotype identical to that of conventional 7 day DC. CD14 down-regulation was paralleled by increased expression of HLA-DR and co-stimulatory molecules, while dextran uptake decreased upon maturation.

We tested the capability of acDC to amplify Ag-specific T cell responses upon pulsing with protein Ags using an ELISpot detection system. After the 24 h maturation period, non-adherent cells were transferred into ELISpot plates coated with an anti-IFN-γ, anti-IL-10, anti-IL-2 or anti-IL-4 capture Ab, and further cultured for 6 h without any further Ag or cytokine supplementation. acDC-driven cultures were much more efficient at eliciting Ag-specific T cell responses as compared to conventional monocyte-driven conditions (i.e., without any cytokine addition). Background responses against irrelevant proteins or Ag diluent alone did not significantly increase. Moreover, acDC were much more effective when matured with pro-inflammatory stimuli, as compared to acDC left immature (i.e., treated with GM-CSF and IL-4 only). The efficiency of acDC was similar to that of conventional 7 day DC and was similarly effective at amplifying different cytokine responses, including IFN-γ, IL-10, IL-2 and IL-4. For example, the median increase in specific signal with acDC matured with TNF-α, PGE2 and IL-1β as compared to monocytes was 2.2-fold (range 1.5-8.7) for IFN-γ and 1.4-fold (range 1.2-5.0) for IL-10.

Example 2

Peptide Ag Stimulation

Material and Methods:

The same experiment as described in Example 1 was carried out, using peptide antigen stimulation instead of protein Ag stimulation. Examples of peptide Ags tested were: Influenza matrix protein $(MP)_{58-66}$, Influenza hemagglutinin $(HA)_{306-318}$, $GAD_{555-567}$, $GAD_{114-123}$, $PI_{B10-18}$. Example of peptides used as negative controls were pyruvate dehydrogenase $(PD)_{5-13}$ and collagen II $(CII)_{261-273}$.

Results:

The signal elicited in acDC cultures pulsed with protein Ags originated exclusively from CD4+ T cells, as it was completely abolished when these cells were removed. Ag-specific CD8+ T cell responses could only be elicited upon longer culture periods (7 days). The same was true when 7 day DC were used to stimulate whole or CD4-depleted PBMCs, thus ruling out an acDC-specific defective feature. This CD4-specific stimulation was not due to inefficient activation of CD8+ T cells, but rather to culture conditions not optimal for eliciting cross-presentation of internalized Ags. Indeed, when peptide epitopes rather than protein Ags were used, both CD4+ and CD8+ T cell responses were triggered, and both were significantly amplified by acDC as compared to monocytes. Thus, we elaborated a variation of the acDC culture technique to expand and detect Ag-specific T cells recognizing a specific peptide epitope. In this case, peptides of interest are added at day 1 along with proinflammatory stimuli. This variation allows to detect both CD4+ and CD8+ T cells specific for a given epitope.

Thus, the acDC culture protocol can be used to stimulate T cells with either protein or peptide Ags.

Example 3 acDC Induction Directly in Blood

Cytokine cocktails and protein/peptide Ags were added as in Example 1 (for protein Ags) or Example 2 (for peptide Ags) directly into freshly drawn heparinized blood samples, without any preliminary PBMC purification or blood dilution. At the end of the 48 h culture, plasma and/or PBMCs were recovered and analyzed for Ag-specific T cell responses by plasma cytokine measurement using ELISA (R&D), cytometric bead array (BD), or Bio-Plex (Biorad) assays, or by Miltenyi cytokine capture assays on the cellular fraction following red blood cell lysis. Also in this case, Ag-specific responses elicited in acDC-driven cultures were higher than those elicited in monocyte-driven ones. Depending on the maturation protocol used, this was true for a number of cytokines tested, including IFN-γ, IL-10, IL-2, IL-6, IL-13, TNF-α, G-CSF, IL-1β.

Example 4

T Cell Expansion, Sorting and Cloning Downstream of the acDC Culture and T Cell Response Analysis The acDC culture system is also suitable: 1) for sorting Ag-specific T cells for further functional characterization (e.g., by RT-PCR techniques); and 2) for generating T cell lines and clones for further analyses.

PBMCs were preliminarily labeled with CFSE (carboxy-fluorescein succinimidyl ester, 0.5-1 μM), subjected to the acDC culture and transferred to ELISpot plates as above. After the 6 h ELISpot incubation, cells were recovered and put back into culture for an additional 5 days without further stimuli. At the end of this culture, proliferating $CFSE^{low}$ cells were single-cell sorted and further expanded through 3 rounds of stimulation using previously described protocols [Mannering et al., J. Immunol. Methods 298:83, 2005]. As an example, a tetanus toxoid (TTX)-specific response was detected by ELISpot with a frequency of 0.044%, which correlated with selection of a TTX-specific $CFSE^{low}$ fraction of 3.0%, corresponding to an expansion of ~68-fold. Also for this in vitro culture, the acDC-based culture proved superior to conventional monocyte-based expansions, which yielded 10-fold less TTX-specific cells (0.29%). The TTX-specific $CFSE^{low}$ fraction was sorted and cloned, yielding TTX-specific $CD4^1$ clones. This approach also confirmed that the responses detected from acDC cultures are indeed Ag-specific.

Example 5

The acDC Culture System Detects β-Cell-Specific CD4+ T-Cell Responses

Type-1 diabetes (T1D) is a T-cell-mediated autoimmune disease targeting insulin-producing β-cells. Its incidence is steadily increasing (up to 15 new diagnoses/100,000/year in France; 3-4% increase in incidence per year). Given its distinctive epidemiology (it mainly affects children and young adults life-long), it is a chronic, costly and invalidating disease, leading to severe complications: cardiovascular disease, nephropathy and end-stage renal disease, retinopathy and blindness.

T1D clinical onset and diagnosis is a late event in the pathogenic cascade, which takes place when the majority of the β-cells have already been destroyed over the previous months/years by autoreactive T cells. At that stage, little space is left for cause-related therapies aimed at correcting immune mechanisms, and insulin replacement is the only therapeutic option. There is therefore an important lack of suitable biomarkers for disease prediction and follow-up, and of appropriate antigen (Ag)-specific therapies capable of selectively turning off β-cell-specific T cell responses while avoiding generalized immune suppression.

For T1D, autoantibodies currently in use have important limitations, as 15% of T1D patients are autoantibody-negative; autoantibodies do not predict time to T1D onset; and they do not change following successful immune interventions.

Alternatively, T cell responses, whether CD8+ T cell responses or CD4+ T cell responses, can be used as early biomarkers.

Cytokine ELISpot is a widely used assay for the investigation of specific immune responses in various conditions. CD8+ T-cell responses can be readily detected by this method. Although the little information available about CD8+ β-cell target epitopes for human T1D remains a limitation, existing techniques for measuring CD8+ T cell responses (ELISpot- and tetramer-based) have given promising results (Toma et al., *Proc. Natl. Acad. Sci. U.S.A.* 102: 10581, 2005; Mallone et al., *Diabetes* 56:613, 2007).

Ag-specific CD4+ T cells are present in peripheral blood at very low frequencies (0.001-0.0001%, even lower than their CD8+ counterparts), making their detection troublesome—particularly in the autoimmune setting.

Alleva et al. (*J Clin Invest.* 107:173, 2001) reported the detection of a cellular response to the insulin B9-23 epitope in T1D patients, using a direct ELISpot assay. Arif et al., (*J Clin Invest.* 113:451, 2004) reported the detection of a cellular response to several proinsulin-derived peptides using an indirect ELISpot assay. In this article, peripheral blood mononuclear cells were incubated with antigenic peptides prior to the ELISpot assay.

However, those studies have been overall difficult to reproduce outside their Laboratories of origin. This underlines the technical hurdles of such procedures, and the overall low sensitivity of these detection systems.

We therefore used the acDC-based procedures described in this application to investigate the β-cell-specific CD4+ T cell responses of T1D. Different groups of patients were considered and several key observations were made: first, T1D adults drawn at diagnosis were characterized by a high prevalence (83.3%) of proinsulin (PI)-specific responses, which contrasted with the rarity of these responses in long-standing patients (5.4%; P<0.0001). On the contrary, GAD-specific responses were similarly represented—although at lower frequencies—irrespective of T1D duration. Second, new-onset T1D children did not display any PI-specific T cell response. Healthy controls (both adults and children) did not display any PI-specific T cell response except in two cases (frequency 8.7%). In both cases, these subjects harbored previously unrecognized T1D risk factors, being positive for the HLA-DR4/DQ8 susceptibility haplotype in one case, and for anti-GAD Abs in the other. At-risk $1^{st}$ degree relatives (n=10; defined as individuals positive for islet-cell Abs, frequently along with other Ab markers) displayed a somehow intermediate picture, with 30.0% of tested individuals positive for PI-specific responses. Importantly, only 1 of the 10 individuals tested has developed T1D until now, and he had been correctly identified as being at high risk of T1D progression by the acDC-based ELISpot assay. Without wishing to be bound by theory, we hypothesize that the difference we observe between new-onset and long-standing T1D patients reflects a regulatory response induced by insulin treatment, with important implications for clinical trials aimed at preventing disease by blocking autoimmune β-cell destruction in at-risk subjects. This regulatory response can in some cases be a natural one independent of insulin therapy, as seen in children.

Example 6

Enhanced Detection of Antigen-Specific T-Cell Responses by Accelerated Co-Cultured Dendritic Cells (acDCs Abstract The detection of antigen (Ag)-specific T cells is often limited by assay sensitivity. Therefore, we devised an approach to enhance Ag processing and presentation to T cells in human and mouse peripheral blood mononuclear cells (PBMCs) by accelerating induction and maturation of dendritic cells (DCs) in situ (referred to as accelerated co-cultured DCs, acDCs). Unfractionated PBMCs or whole blood were incubated for 48 h with protein or peptide Ag and cytokine cocktails to rapidly and sequentially induce, pulse and mature acDCs. Simultaneously, Ag was processed and/or presented to neighboring T cells, thus telescoping multiple steps leading to T-cell activation and minimizing time, manipulation and blood requirements. Elicited T-cell responses were Ag-specific, as detected by different readouts (cytokine secretion, proliferation, CD137 upregulation, binding of human leukocyte Ag multimers). acDC-based assays may find valuable applications for monitoring T-cell responses in different settings, such as in viral, tumor and autoimmune diseases.

Introduction

Despite the central role of T cells in mounting responses against different foreign and self antigens (Ags), routine diagnostic detection of immune-mediated processes, e.g. in infectious or autoimmune diseases, relies largely, if not exclusively, on measurement of antibody (Ab) responses. However, Abs do not always mediate or reflect underlying pathology and may be poorly informative when the immune process is predominantly T-cell-mediated (1). The sole reliable clinical application of Ag-specific T-cell assays to date has been in the diagnosis of *M. tuberculosis* infection (2). Moreover, the importance of effectively measuring T-cell immunity reaches beyond diagnostic applications (3). T-cell monitoring is also required to evaluate immune modulation therapies aimed at boosting viral or tumor-specific immunity, or at quenching immunity against self (4) or transplanted (5) tissues. T-cell screening tools to assess the immunogenic potential of replacement proteins (e.g. coagulation factors) (6) or of vaccines (7) are equally demanded.

The lack of routine human T-cell assays is due to intrinsic difficulties in measuring T-cell responses. T cells specific for a given Ag are present at a very low frequency in blood (i.e. 0.1-0.001%) (8). Although these cells are sometimes detectable ex vivo, their rarity challenges the sensitivity of technologies such as enzyme-linked immunospot (ELISpot) and flow cytometry. Alternatively, the frequency of these cells may be augmented by preliminary expansion steps, but these require additional time and manipulation. Epitope peptides that bind to human leukocyte Ag (HLA) molecules for presentation and recognition by the T-cell receptor are frequently used to elicit T-cell responses, as they do not require processing by Ag-presenting cells (APCs). While bypassing this first limiting step for T-cell activation, epitopes nevertheless need to be preliminarily identified as binding to specific HLA molecules to stimulate T cells. Furthermore, peptides stimulate a limited repertoire of T-cell responses against selected Ag sequences.

Dendritic cells (DCs) are specialized APCs endowed with unrivaled processing and stimulatory properties (9). These features make them attractive for boosting T-cell activation, thus enhancing detection of Ag-specific T cells in vitro. To this end, DCs are routinely induced from monocyte precursors, a procedure which most commonly requires a 6 day differentiation with granulocyte/macrophage colony-stimulating factor (GM-CSF) and interleukin (IL)-4 (10,11), and subsequent maturation for at least another day with a range of proinflammatory stimuli to achieve full T-cell stimulatory capacity (10-12). These time requirements are not compatible with clinical laboratory practice. Although shorter protocols have been described (13), they still require preliminary isolation of CD14+ monocytes, thus greatly increasing blood requirements and hands-on work.

To overcome these limitations, we asked whether DCs could be induced and matured to promote Ag presentation and T-cell activation in situ in peripheral blood mononuclear cells (PBMCs). The advantage of this approach would be two-fold. On one hand, it would reduce time, purification steps and blood needs. On the other, it would keep lymphocytes in contact with differentiating DCs, thus stimulating T cells as Ag processing, presentation and DC maturation occurred. As these DCs are induced and Ag-pulsed within 48 h while surrounded by cognate T lymphocytes and other blood cells, they are referred to as accelerated co-cultured DCs (acDCs). Consequently, we developed an efficient, short-term procedure which amplifies Ag-specific T-cell responses detected with a variety of assay platforms.

Results acDCs Amplify Ag-Specific T-Cell Responses

To investigate whether acDCs could amplify the Ag-specific responses of co-cultured T cells, acDCs were induced within PBMC mixtures by GM-CSF and IL-4 for 24 h. At the same time, different protein Ags [e.g. tetanus toxoid (TTX), M. tuberculosis purified protein derivative (PPD), hexavalent vaccine or no Ag] were added from the start of culture. After additional 24 h of maturation, non-adherent cells were transferred into enzyme-linked immunospot (ELISpot) plates coated with anti-interferon (IFN)-γ capture Abs, and further cultured for 6 h without additional Ag or cytokine supplementation (for a schematic, see FIG. 7).

In order to select the most suitable maturation protocols, we first compared the stimulatory potential of acDCs matured with different stimuli with that of PBMCs cultured in the absence of cytokines (FIG. 1a). ELISpot IFN-γ responses were significantly amplified by acDCs matured by different protocols. The most effective were tumor necrosis factor (TNF)-α/prostaglandin (PG)E2/IL-1β (42.0% signal increase over PBMCs only, p=0.03), polyinosinic:polycytidylic acid (polyI:C) (69.3% signal increase; p<0.001), lipopolysaccharide (LPS; 55.2% increase, p=0.01), and anti-CD40/IFN-α (170% increase, p<0.001). Importantly, all these protocols increased the Ag-specific IFN-γ signal but not the background, thus ruling out non-specific T-cell activation by cytokines. Lack of upregulation of activation markers (i.e. CD69, CD25, CD137) in T cells from PBMCs exposed or not to cytokines in the absence of Ag further excluded non-specific activation (data not shown; for CD137, see FIG. 5). Other maturation cocktails were excluded either because they did not amplify the Ag-specific signal (TNF-α/PGE2, CpG oligodeoxynucleotides, polyI:C/PGE2, anti-CD40, anti-CD40/IFN-γ) or because they did so together with a significant increase in background (anti-CD40/IL-1β).

Human acDCs were not only able to amplify IFN-γ-secreting responses but also other cytokine responses detected by ELISpot (FIG. 1b-d). While anti-CD40/IFN-α maturation amplified IFN-γ responses the most (2.7-fold), TNF-α/PGE2/IL-1β was the only combination that boosted all cytokine responses tested (1.2-, 50.0- and 2.9-fold for IFN-γ, IL-10 and IL-4, respectively). These two maturation cocktails were therefore retained. IL-17 responses were not amplified by any of these protocols (data not shown). Moreover, only TTX memory responses, not naïve responses to the KLH neoAg, were significantly above background (FIG. 1b-d).

Amplification of T-cell responses by acDCs were also obtained with mouse blood mononuclear cells incubated with GM-CSF/IL-4 followed by LPS for maturation. Cells from mice immunized with a single low dose of keyhole limpet hemocyanin (KLH) displayed significantly higher KLH-specific IFN-γ ELISpot recall responses in the presence of the acDC cytokines (FIG. 8).

Characterization of acDCs revealed a phenotype identical to that of conventional monocyte-derived DCs (moDCs) (FIG. 2a). CD14 down-regulation was paralleled by increased expression of HLA-DR and co-stimulatory molecules, while dextran uptake, although more efficient in moDCs, decreased upon maturation. acDCs were also at least as efficient as moDCs at eliciting Ag-specific T-cell responses (FIG. 2b). As expected, both acDCs and moDCs were more effective following maturation with proinflammatory stimuli (FIG. 2b).

Reproducibility of acDC-Amplified T-Cell Responses

Reproducibility was assessed by testing different frozen cell aliquots from the same PBMC preparation (i.e. inter-assay variability at the analytical level, which excludes differences introduced by blood drawing and processing; FIG. 2c), and different PBMC preparations derived from blood draws taken on different occasions from the same individual (i.e. inter-assay variability at the pre-analytical and analytical level, which includes differences due to blood drawing and processing; FIG. 2d). In both cases, assay variability was <10%. Notably, variation between fresh and frozen samples (6.9%) was also small (FIG. 2e).

Ag-Specific T Cells Expanded by acDCs Can Be Isolated and Cloned

To select and expand Ag-specific T cells, dilution of a cell-bound dye, carboxy-fluorescein diacetate succinimidyl ester (CFSE), was used as a readout of proliferation (14) and combined with the acDC procedure (FIG. 3a). PBMCs were first labeled with CFSE and then used in the acDC-amplified ELISpot procedure. They were recovered from the ELISpot plate and cultured for another 6-8 days without further manipulation. Proliferating (CFSElow) cells were then identified by flow cytometry, sorted into single cells and further expanded through three rounds of stimulation with anti-CD3 Ab, IL-2 and IL-4 (15). A representative example is shown in FIG. 3b-d. A TTX-specific IFN-γ ELISpot response was detected (441 IFN-γ spot-forming cells (SFC)/106 PBMCs; 0.044%) (FIG. 3b), which gave rise to a TTX-specific CFSElow fraction of 3.0%, corresponding to an expansion of ~68-fold. The acDC condition was superior to conventional expansion in the absence of cytokines, which yielded 10-fold less TTX-specific cells (0.29%, p<0.001). No significant increase in background proliferation was observed (FIG. 3c). The TTX-specific CFSElow fraction (divided cells) was sorted and cloned, generating TTX-specific T-cell clones, as assessed by recall assay on TTX- vs. control-pulsed DCs (FIG. 3d).

Similar expansions were obtained after stimulation with peptide epitopes and detection by peptide-HLA multimer-stained CD4+ or CD8+ T cells (FIG. 9). Fresh PBMCs were stained with HLA multimers ex vivo and at 48 h and 7 d after stimulation with peptide in the absence or presence of acDCs. HLA-A2-restricted Flu MP58-66-specific CD8+ T cells detected ex vivo (0.063% after subtraction of background staining) (FIG. 9a) were expanded after 7 d, but not after 48 h, of peptide-specific stimulation (13.3-fold expansion vs. 0.54-fold in the absence of cytokines) (FIG. 9b). Similar results were obtained by analyzing Flu HA306-318-specific HLA-DR4-restricted CD4+ T cells. The frequency of peptide-specific CD4+ T cells ex vivo (0.24% after background subtraction) (FIG. 9c) increased upon peptide-specific expansion only after 7 d of culture, and only when the acDC cocktail was used (13.5-fold expansion vs. 0.79-fold in the absence of cytokines) (FIG. 9d). Together, these data show that acDCs significantly enhance expansion of Ag-specific T cells upon prolonged culture and that acDC-amplified T-cell responses are Ag-specific.

Protein and Peptide Ags Trigger Different T-Cell Responses

Next, we compared T-cell stimulation by acDCs pulsed with protein and peptide Ags. When protein Ags were used, the responses elicited in 48 h acDC cultures followed by IFN-γ ELISpot originated exclusively from CD4+ T cells, as their depletion either at start or at end of stimulation completely abolished responses (FIG. 4a). The same was true with moDCs, demonstrating that this feature was not peculiar to acDCs. Weak CD8+ T-cell activation was likely due to inefficient cross-presentation of Ags taken up during the 48 h culture. Thus, when protein Ags were replaced by HLA Class II- or Class I-restricted peptide epitopes, CD4+ and CD8+ T-cell responses were triggered, respectively (FIG. 4b), again confirmed by CD4+ and CD8+ T-cell depletion (not shown). Moreover, both types of responses were significantly amplified by acDCs compared to conventional PBMCs (3.2- and 6.3-fold for CD4+ and CD8+ T cells, respectively; p<0.05), demonstrating the utility of the acDC technique for both protein and peptide Ags.

Ag-specific CD4+ T cells detected by acDC-amplified ELISpot were predominantly memory cells, as depletion of CD45RO+ (but not of CD45RA+) T cells significantly reduced the response (81.4% decrease, p<0.05; FIG. 4c). This was confirmed by comparing responses to the recall Ag TTX with those to the neoAg KLH. Indeed, KLH did not elicit significant IFN-γ or IL-10 T-cell responses during the 48 h acDC stimulation (FIG. 4d). However, when these cells (which had first been CFSE-labeled) were cultured for another week, a low-grade KLH-specific CD4+ response was detected (FIG. 4e). Moreover, TTX-specific CD8+ T cells were also observed, suggesting that cross-priming occurred with longer stimulation.

acDCs Enhance Different T-Cell Responses in Either PBMCs or Whole Blood

We further investigated whether acDC amplification applied to other functional T-cell readouts using purified PBMCs. IFN-γ secretion was detected by a capture assay (Miltenyi) with bi-specific mAbs against CD45 (which bind to the surface of immune cells) and IFN-γ (FIG. 5a). No significant TTX-specific IFN-γ secretion was detected in the absence of cytokines However, IFN-γ was detected on both CD4+ and CD8+ T cells after acDC amplification, with no increase in background. The number of IFN-γ+ T cells was higher than detected by ELISpot, which may explain why CD8+ T-cell responses were also visualized. Similar results were obtained with surface expression of CD137, a marker of T-cell activation) (16,17) (FIG. 5b). Both readouts were also compatible with downstream sorting and cloning of Ag-specific T cells (data not shown).

Next, we asked whether acDCs could amplify Ag-specific T-cell responses in whole blood. These experiments were performed in parallel to those on purified PBMCs shown in FIG. 5b, using the same blood draw, by adding the acDC cocktail (GM-CSF/IL-4 followed by anti-CD40/IFN-α) directly to undiluted heparinized blood (250 µl) along with Ag. After 48 h, hemolysed blood was interrogated for T-cell activation by flow cytometric analysis of CD137 expression (FIG. 5c). CD137 upregulation was more sensitively detected on whole blood than on purified PBMCs when no cytokines were added, while the opposite was true for acDC conditions. The lower amplification obtained by acDCs on whole blood was nonetheless sufficient to enhance CD4+, but not CD8+, T-cell responses.

acDCs Amplify Ag-Stimulated Cytokine Secretion in Whole Blood

Finally, we explored whether acDC amplification could detect Ag-specific bulk cytokine secretion on plasma collected after whole blood stimulation. To this end, heparinized whole blood was incubated with the acDC cocktail (GM-CSF/IL-4 followed by anti-CD40/IFN-α) and Ag as above. After 48 h, plasma supernatants were recovered for cytokine measurements. Several cytokines displayed significant increases upon Ag stimulation (FIG. 6a). Except for macrophage inflammatory protein (MIP)-1α, the net (i.e. background subtracted) Ag-specific signal was higher in the acDC than in the "no cytokine" condition for all markers (median signal amplification 6.1-fold; range 3.6-41.9; p<0.001). Importantly, basal secretion did not increase upon acDC exposure and even decreased in some instances, pointing to an Ag-specific amplification effect. As for CD137 upregulation, we compared the sensitivity of cytokine detection in whole blood and PBMCs (FIG. 6b). Cytokines were detected at greater sensitivity with PBMCs than whole blood, median concentrations being ~4-fold higher with PBMCs (range 1.0-34.0; p<0.001).

Surprisingly, some cytokines not known to be secreted by T cells (G-CSF, IL-β) also behaved as markers of Ag-specific activation. Intracellular cytokine staining further showed that Ag-specific IL-10 secretion derived from adherent cells and not from non-adherent ones (FIG. 10).

Discussion

The therapeutic potential of DCs is being actively explored to induce immunogenic or tolerogenic T-cell responses to disease-related Ags (18, 19). However, despite their potent Ag processing and presenting properties, DCs have not been exploited for T-cell diagnostics. This is probably due to constraints dictated by the low frequency of accessible circulating DCs and by the large blood volumes required to generate DC-type APCs starting from monocytes and other precursors.

The acDC technique fills this gap, by providing the means to amplify Ag-specific T-cell responses in a short, simple method amenable to routine laboratory application. Side-by-side comparison of acDCs and moDCs revealed striking similarities, both in terms of phenotype and of stimulatory potency. The notable advantage of acDCs is that they are generated in situ within 48 h in the more physiological setting of unfractionated PBMCs or whole blood. Furthermore, sample requirements are minimal, with only $10^6$ PBMCs (~1 ml of blood) or 250 µl of whole blood required. This is a critical consideration in longitudinal monitoring of T-cell responses, especially in children, and a decided advantage in screening peptide libraries for T-cell epitopes.

In bulk culture, induction and Ag pulsing of acDCs is coupled with simultaneous activation—in an Ag-specific fashion—of T cells, thus lining up three critical steps leading to a T-cell response. A potential problem in this type of assay is non-specific T-cell activation by the cytokines used to induce and mature acDCs. This was however not the case, as the basal values for T-cell readouts (proliferation, CD137 upregulation, cytokine secretion) were only marginally affected by the acDC protocol. It is relevant that limited (up to 10-fold) increases in background values do not preclude detection of rare (0.001% frequency) T-cell responses, as previously demonstrated (20). It is possible that cross-talk between Ag-presenting acDCs and responding T cells further synergizes to amplify Ag-specific responses. Responses detected in acDC-based assays were bona fide Ag-specific, as sorted T cells expanded in vitro preserved Ag specificity. On the other hand, HLA-peptide epitope multimer studies demonstrated that T-cell precursor frequencies did not increase until after the first 48 h of acDC-driven Ag stimulation. Nevertheless, the number of activated (CD137+) T cells was already increased at 48 h. This suggests that Ag-specific responses, as detected by functional readouts, are magnified and revealed by bystander activation mechanisms. For research settings requiring exact enumeration of T-cell precursor frequencies, CFSE dilution could be coupled with HLA multimer staining to determine the original number of proliferating T cells (21). For routine clinical applications, amplified readouts as obtained within 48 h would suffice.

The acDC technique serves both whole protein Ags and peptide epitopes. Protein Ags eliminate the need for epitope identification and patient selection based on HLA type. Moreover, they allow stimulation with the whole repertoire of processed epitopes. Given the high endocytic and Ag-processing capacity of DCs, acDC assays in which cellular material such as donor, tumor or autoimmune-targeted tissues are used as Ag sources could also be envisioned. Stimuli used to mature acDCs were also a critical parameter. As previously reported (12), anti-CD40 and IFN-α along with GM-CSF/IL-4 more efficiently amplified IFN-γ-producing T helper (Th)1 responses, while combining TNF-α and IL-1β with PGE2 (22) led to a more balanced T-cell phenotype allowing for better detection of Th2 (IL-4) and T regulatory (IL-10) responses.

The acDC technique is compatible with a wide range of T-cell readouts, some of which can be complemented with downstream sorting of Ag-specific cells for further expansion and/or characterization. The versatility of the acDC technique was exemplified by single-cell (cytokine ELISpot, CFSE proliferation, IFN-γ capture, CD137 upregulation, HLA multimers) and bulk (cytokines in plasma or culture supernatants) assays. The sensitivity of these different acDC assay formats will need to be evaluated for each application. Single-cell assays are often preferred, as they provide information about the frequency and phenotype of responding T cells and are frequently more sensitive than bulk assays. Nonetheless, bulk assays are easier to perform in a routine setting, and their detection sensitivity may be sufficient for many applications, as in the case of IFN-γ enzyme-linked immunosorbent assays for *M. tuberculosis* (23). Similarly, assays employing whole blood avoid PBMC purification, thus keeping cells in a more physiological milieu and offering further convenience. Although cytokines from acDC cultures were apparently detected with greater sensitivity with PBMCs than whole blood, the difference may in part be due to the different cells and their concentrations in blood and PBMCs. Indeed, PBMCs were resuspended at the optimal concentration of $5 \times 10^3$ cells/µl, whereas whole blood volumes of 250 µl/sample corresponded to ~$1 \times 10^3$ PBMCs/µl. Hence, purified PBMCs were ~5 times more concentrated than blood cells.

An interesting result from bulk assays was stimulated secretion of G-CSF and IL-1β, that are not derived from T cells. It is likely that these cytokines were produced by adherent APCs, as suggested by IL-1β ELISpot assays performed on adherent and non-adherent cells. A positive feedback loop between Ag-presenting acDCs and responding T cells may further activate acDCs, inducing them to secrete signature cytokines in an Ag-specific fashion. APC-derived cytokines may thus constitute valuable indirect biomarkers of T-cell responses.

Skewing the acDC phenotype in vitro may also offer ways of inducing Ag-specific T cells with different properties. For example, IL-10-treated DCs are tolerogenic and can give raise to CD4+ and CD8+ T cells with regulatory properties (24, 25). acDC stimulation in the presence of IL-10 thus offers a strategy to obtain Ag-specific T regulatory cells.

Methods

Antigens. The following Ags were used: bovine serum albumin (BSA; Sigma, Lyon, France), TTX (a kind gift of Dr. Rino Rappuoli, Novartis, Siena, Italy), *M. tuberculosis* PPD (Tubertest, Sanofi Pasteur, Lyon, France), hexavalent vaccine (Infanrix hexa, GlaxoSmithKline, Rixensart, Belgium) and KLH (Sigma). Ag purity was confirmed by SDS-PAGE, and endotoxin concentration was <0.035 EU/µg by Limulus lysate assay (Lonza, Saint Beauzire, France). Peptides Flu MP58-66 and Flu HA306-318 were >95% pure (GL Biochem, Shanghai, China).

Induction of acDCs in PBMCs. The study was approved by Ethics Committees and all subjects gave written informed consent. PBMCs were isolated and either used fresh or frozen as described (26). On day 0, PBMCs were plated ($10^6$ cells/100 µl/well) in 96-well flat-bottomed plates in AIM-V medium supplemented with 1000 U/ml GM-CSF, 500 U/ml IL-4 (R&D, Lille, France) and containing protein Ags (0.1-10 µg/ml). After 24 h (day 1), maturation stimuli were added, comprising the following reagents in different combinations (see FIG. 1c): 1000 U/ml TNF-α, 10 ng/ml IL-1β, 1000 U/ml IFN-γ (all from R&D), 1 µM PGE2 (Calbiochem, San Diego, Calif.); CpG ODN2216 (5 µg/ml; Cell Sciences, Canton, Mass.), polyI:C (20 µg/ml; Cayla/InvivoGen, Toulouse, France), LPS (100 ng/ml; from *E. coli* O55:B5, Sigma), anti-CD40 Ab (10 µg/ml; clone G28.5, produced in-house), IFN-α-2a (1000 U/ml; Roferon-A, Roche, Neuilly-sur-Seine, France). Maturation cocktails used in each experiment are detailed in figure legends. IL-7 (0.5 ng/ml; R&D) was added along with maturation stimuli (26). When used, peptide Ags were added on day 1 along with maturation stimuli. On day 2 (48 h after start of culture), non-adherent cells were collected, washed and analyzed.

Induction of acDCs in whole blood. Fresh, undiluted heparinized blood (250 µl) was dispensed in 1.5 ml tubes, cytokines and Ags added as for PBMC stimulation, and hemolysed blood and/or plasma supernatants analyzed after 48 h.

DC characterization. To generate moDCs, purified monocytes were cultured with GM-CSF/IL-4 for 6 d and matured with TNF-α/PGE2/IL-1β for additional 24 h. Phenotypes of acDCs and 7 d moDCs were determined by staining with Abs specific for HLA-DR, CD14, CD80, CD86 and CD11c (BD). Endocytotic activity was assessed by dextran-FITC fluorescence uptake. Flow cytometry experiments were performed on a FACSAria equipped with 488, 633 and 407 nm lasers (BD).

ELISpot assays. Following 48 h incubation of acDCs in PBMCs, non-adherent cells were washed, resuspended in fresh AIM-V and assayed for 6 h as described (27). Spots were counted on a Bioreader 5000 Pro-SF (BioSys, Karben, Germany) and means of 3-6 replicates determined. ELISpot readouts are expressed as SFC/$10^6$ PBMCs and are background-subtracted (for spontaneous responses in the presence of BSA or no Ag, which were identical in all cases)(27).

CFSE assays and T-cell cloning. PBMCs were stained with 0.1 µM CFSE (Invitrogen/Molecular Probes) and used for acDC cultures as described above. After 2 d, non-adherent cells were washed, transferred to EliSpot plates for 6 h, then replated in 96-well U-bottom plates. Following 5-8 d of culture, cells were stained for CD4/CD8. A single CD4+ CFSEdim cell was sorted into each well of a 96-well U-bottom plate. Each well contained IL-2 (20 U/ml; R&D), IL-4 (5 ng/ml), anti-CD3 (OKT3, 30 ng/ml) and $2\times10^5$ irradiated PBMCs from two unrelated donors (15). Cells were fed every 7 days with fresh cytokines Growing clones were tested after ~3 weeks by intracellular IFN-γ staining after incubation with Ag-pulsed or unpulsed moDCs.

IFN-γ capture and CD137 upregulation assays. IFN-γ capture was performed using a Miltenyi IFN-γ-allophycocyanin kit. CD137 was stained with phycoerithrin (PE)-labeled 4B4 Ab (BD).

HLA multimer assays. PE-labeled HLA-A0201 pentamers loaded with Flu MP58-66 or control peptide (ProImmune, Oxford, UK) were used according to the manufacturer's instructions. PE-labeled HLA-DR0401 tetramers loaded with Flu HA306-318 or control peptide were kindly provided by Drs. E. James and G. T. Nepom (Benaroya Research Institute, Seattle, Wash.) and used as described (28).

Mouse acDC stimulation. Balb/c mice were subcutaneously immunized with 50 µg KLH in complete Freund's adjuvant at the base of the tail. After 14 d, blood cells were harvested, hemolysed and plated in 48-well plates ($2\times10^6$ cells/well). Mouse GM-CSF and IL-4 (R&D) were added as for human acDCs, with or without KLH (0.1 µg/ml); LPS (10 ng/ml) was added at day 1 and ELISpot assays performed on day 2 as described (27).

Cytokine multiplex assays. Supernatants from 48 h acDC cultures were analyzed on a Luminex platform (Bio-Plex 200, Bio-Rad, Gladesville, NSW, Australia) using a Milliplex panel (Millipore/Abacus, Brisbane, QLD, Australia) comprising the following cytokines and chemokines: G-CSF, GM-CSF, IFN-γ, IL-1β, IL-2, IL-6, IL-8, IL-10, IL-13, IL-17, MIP-1α, MIP-1β and TNF-α.

Statistical analyses. All graphs are displayed as means±SEM of ≥3 independent experiments. All statistical analyses were two-tailed and performed according to variable distribution and sample size using GraphPad Prism 5 (La Jolla, Calif.).

References of Example 6

1. Harrison, L. C. et al. Islet-reactive T cells are a marker of preclinical insulin-dependent diabetes. *J. Clin. Invest* 89, 1161-1165 (1992).

2. Lalvani, A. et al. Enhanced contact tracing and spatial tracking of *Mycobacterium tuberculosis* infection by enumeration of antigen-specific T cells. *Lancet* 357, 2017-2021 (2001).

3. Kern, F., Lipira, G., Gratama, J. W., Manca, F., & Roederer, M. Measuring Ag-specific immune responses: understanding immunopathogenesis and improving diagnostics in infectious disease, autoimmunity and cancer. *Trends Immunol.* 26, 477-484 (2005).

4. Roep, B. O. & Peakman, M. Surrogate end points in the design of immunotherapy trials: emerging lessons from type 1 diabetes. *Nat. Rev. Immunol.* 10, 145-152 (2010).

5. Ashton-Chess, J., Giral, M., Soulillou, J. P., & Brouard, S. Can immune monitoring help to minimize immunosuppression in kidney transplantation? *Transpl. Int.* 22, 110-119 (2009).

6. Dasgupta, S. et al. Auditing protein therapeutics management by professional APCs: toward prevention of immune responses against therapeutic proteins. *J. Immunol.* 181, 1609-1615 (2008).

7. Keilholz, U., Martus, P., & Scheibenbogen, C. Immune monitoring of T-cell responses in cancer vaccine development. *Clin. Cancer Res.* 12, 2346s-2352s (2006).

8. Mallone, R. & Nepom, G. T. MHC Class II tetramers and the pursuit of antigen-specific T cells: define, deviate, delete. *Clin. Immunol.* 110, 232-242 (2004).

9. Shortman, K. & Liu, Y. J. Mouse and human dendritic cell subtypes. *Nat. Rev. Immunol.* 2, 151-161 (2002).

10. Sallusto, F. & Lanzavecchia, A. Efficient presentation of soluble antigen by cultured human dendritic cells is maintained by granulocyte/macrophage colony-stimulating factor plus interleukin 4 and downregulated by tumor necrosis factor alpha. *J. Exp. Med.* 179, 1109-1118 (1994).

11. Zhou, L. J. & Tedder, T. F. CD14+ blood monocytes can differentiate into functionally mature CD83+ dendritic cells. *Proc. Natl. Acad. Sci. U. S. A.* 93, 2588-2592 (1996).

12. Luft, T. et al. IFN-alpha enhances CD40 ligand-mediated activation of immature monocyte-derived dendritic cells. *Int. Immunol.* 14, 367-380 (2002).

13. Dauer, M. et al. Mature dendritic cells derived from human monocytes within 48 hours: a novel strategy for dendritic cell differentiation from blood precursors. *J. Immunol.* 170, 4069-4076 (2003).

14. Mannering, S. I. et al. A sensitive method for detecting proliferation of rare autoantigen-specific human T cells. *J. Immunol. Methods* 283, 173-183 (2003).

15. Mannering, S. I. et al. An efficient method for cloning human autoantigen-specific T cells. *J. Immunol. Methods* 298, 83-92 (2005).

16. Wolfl, M. et al. Activation-induced expression of CD137 permits detection, isolation, and expansion of the full repertoire of CD8+ T cells responding to antigen without requiring knowledge of epitope specificities. *Blood* 110, 201-210 (2007).

17. Wehler, T. C. et al. Rapid identification and sorting of viable virus-reactive CD4(+) and CD8(+) T cells based on antigen-triggered CD137 expression. *J. Immunol. Methods* 339, 23-37 (2008).

18. Dhodapkar, M. V. et al. Rapid generation of broad T-cell immunity in humans after a single injection of mature dendritic cells. *J. Clin. Invest* 104, 173-180 (1999).

19. Hackstein, H., Morelli, A. E., & Thomson, A. W. Designer dendritic cells for tolerance induction: guided not misguided missiles. *Trends Immunol.* 22, 437-442 (2001).

20. Martinuzzi, E. et al. The frequency and immunodominance of islet-specific CD8+ T-cell responses change after type 1 diabetes diagnosis and treatment. *Diabetes* 57, 1312-1320 (2008).

21. Novak, E. J., Liu, A. W., Nepom, G. T., & Kwok, W. W. MHC class II tetramers identify peptide-specific human CD4 (+) T cells proliferating in response to influenza A antigen. *J. Clin. Invest* 104, R63-R67 (1999).

22. Kalinski, P., Schuitemaker, J. H., Hilkens, C. M., & Kapsenberg, M. L. Prostaglandin E2 induces the final maturation of IL-12-deficient CD1a+ CD83+ dendritic cells: the levels of IL-12 are determined during the final dendritic cell maturation and are resistant to further modulation. *J. Immunol.* 161, 2804-2809 (1998).

23. Mori, T. et al. Specific detection of tuberculosis infection: an interferon-gamma-based assay using new antigens. *Am. J. Respir. Crit Care Med.* 170, 59-64 (2004).

24. Steinbrink, K., Graulich, E., Kubsch, S., Knop, J., & Enk, A. H. CD4(+) and CD8(+) anergic T cells induced by interleukin-10-treated human dendritic cells display antigen-specific suppressor activity. *Blood* 99, 2468-2476 (2002).

25. Gregori, S., Magnani, C. F., & Roncarolo, M. G. Role of human leukocyte antigen-G in the induction of adaptive type 1 regulatory T cells. *Hum. Immunol.* 70, 966-969 (2009).

26. Martinuzzi, E. et al. Serum-free culture medium and IL-7 costimulation increase the sensitivity of ELISpot detection. *J. Immunol. Methods* 333, 61-70 (2008).

27. Mallone, R. et al. CD8+ T-cell responses identify beta-cell autoimmunity in human type 1 diabetes. *Diabetes* 56, 613-621 (2007).

28. Mallone, R. et al. Functional avidity directs T-cell fate in autoreactive CD4+ T cells. *Blood* 106, 2798-2805 (2005).

REFERENCES

Throughout this application, various references describe the state of the art to which this invention pertains. The disclosures of these references are hereby incorporated by reference into the present disclosure.

The invention claimed is:

1. A method for stimulating antigen (Ag) -specific T cell responses in a blood or un-fractionated peripheral blood mononuclear cell (PBMC) sample isolated from a subject, comprising the following steps:
 a) culturing said blood sample or un-fractionated PBMC sample in a medium which induces the differentiation of dendritic cells (DC);
 b) optionally, maturing said DC;
 wherein an Ag is added during steps a) and/or b).

2. A method for diagnosing a disease in a subject comprising the following steps:
 a) culturing a blood sample or an un-fractionated PBMC sample obtained from said subject in a medium which induces the differentiation of DC;
 b) optionally, maturing said DC;
 c) detecting T cell responses;
 wherein one or more disease-associated Ag are added during steps a) and/or b).

3. A method for monitoring the effects of an immune therapy in a subject suffering from a disease comprising the following steps:
 a) culturing a blood sample or an un-fractionated PBMC sample obtained from said subject in a medium which induces the differentiation of DC;
 b) optionally, maturing said DC;
 c) detecting T cell responses;
 wherein one or more disease-associated Ag are added during steps a) and/or b).

4. A method according to claim 2, wherein said disease is selected from the group consisting of autoimmune diseases, such as type 1 diabetes (T1 D), Wegener's granulomatosis, Crohn's disease, celiac disease and multiple sclerosis; cancer disease, such as melanoma, colon cancer, renal cancer and haematological malignancies leukemias, lymphomas and multiple myeloma; infectious diseases caused by infectious agents such as *M. tuberculosis*, HIV, hepatitis C virus, cytomegalovirus, Epstein-Barr virus, influenza viruses; and graft-vs-host disease.

5. A method for evaluating the immunogenicity of a therapeutic protein comprising the following steps:
 a) culturing a blood sample or an un-fractionated PBMC sample in a medium which induces the differentiation of DC;
 b) optionally, maturing said DC;
 c) detecting T cell responses;
 wherein said therapeutic protein is added during steps a) and/or b).

6. A method for screening candidate Ags or epitopes comprising the following steps:
 a) culturing a blood sample or an un-fractionated PBMC sample in a medium which induces the differentiation of DC;
 b) optionally, maturing said DC;
 c) detecting T cell responses;
 wherein a candidate Ag or epitope is added during steps a) and/or b).

7. A method for producing T cell clones displaying specific immunological properties from a subject comprising the following steps:
 a) culturing a blood sample or an un-fractionated PBMC sample obtained from said subject in a medium which induces the differentiation of DC;
 b) optionally, maturing said DC;
 c) isolating at least one T cell displaying said specific immunological properties;
 wherein an Ag is added during steps a) and/or b).

8. A method for generating Ag-specific T regulatory cells displaying specific immunological properties from a subject comprising the following steps:
 a) culturing a blood sample or an un-fractionated PBMC sample obtained from said subject in a medium which induces the differentiation of DC with tolerogenic properties;
 b) optionally, maturing said DC;
 c) isolating at least one T cell displaying said specific immunological properties;
 wherein an Ag is added during steps a) and/or b).

9. A method according to claim 1, wherein said medium which induces the differentiation of DC comprises Granulocyte Macrophage Colony Stimulating Factor (GM-CSF) and/or Flt-3 ligand.

10. A method according to claim 9, wherein said medium which induces the differentiation of DC further comprises interleukin 4 (IL-4).

11. A method according to claim 1, wherein step a) is carried out for an amount of time t(a) comprised between about 16 hours and about 7 days.

12. A method according to claim 1, wherein step b) is carried out in the presence of at least one pro-inflammatory stimuli and/or agent which mimics a viral or bacterial aggression selected from the group consisting of Tumor Necrosis Factor alpha (TNF-α), interleukin-1 beta (IL-1 β), prostaglandin E2 (PGE2), anti-CD40 antibody, interferon-alpha 2a (IFN-α2a), lipopolysaccharides (LPS), polyinosinic:polycytidylic acid (poly I:C), interferon-gamma (IFN-γ), interleukin-7 (IL-7) and mixtures thereof.

13. A method according to claim 1, wherein said method comprises a step b).

14. A method according to claim 13, wherein step b) is carried out for an amount of time t(b) comprised between about 12 and about 72 hours.

15. A method according to claim 1, wherein said biological sample is an un-fractionated PBMC sample.

16. A method according to claim 1, wherein said biological sample is a blood sample.

17. A method according to claim 11, wherein step a) is carried out for an amount of time t(a) comprised between about 20 hours and about 4 days.

18. A method according to claim 11, wherein step a) is carried out for about 24 hours.

19. A method according to claim 14, wherein step b) is carried out for an amount of time t(b) comprised between about 16 and about 48 hours.

20. A method according to claim 14, wherein step b) is carried out for about 24 hours.

* * * * *